(12) United States Patent
Komatsu et al.

(10) Patent No.: US 7,696,245 B2
(45) Date of Patent: Apr. 13, 2010

(54) FLUORESCENT PROBE FOR ZINC

(75) Inventors: Kensuke Komatsu, Tokyo (JP); Tomoya Hirano, Tokyo (JP); Kazuya Kikuchi, Kanagawa (JP); Tetsuo Nagano, 28-15, Amanuma 1-chome, Suginami-ku, Tokyo 167-0032 (JP)

(73) Assignees: Sekisui Medical Co., Ltd., Tokyo (JP); Tetsuo Nagano, Tokyo (JP)

( * ) Notice: Subject to any disclaimer, the term of this patent is extended or adjusted under 35 U.S.C. 154(b) by 1480 days.

(21) Appl. No.: 10/767,334

(22) Filed: Jan. 30, 2004

(65) Prior Publication Data
US 2005/0037332 A1   Feb. 17, 2005

(30) Foreign Application Priority Data
Mar. 28, 2003   (JP) .............................. 2003-089987

(51) Int. Cl.
A61K 31/353 (2006.01)
C07D 311/80 (2006.01)
(52) U.S. Cl. .................. 514/455; 549/391
(58) Field of Classification Search .............. 514/455; 549/391
See application file for complete search history.

(56) References Cited
U.S. PATENT DOCUMENTS

| | | | |
|---|---|---|---|
| 4,891,075 A | 1/1990 | Dakubu et al. |
| 4,968,631 A | 11/1990 | Dakubu |
| 5,037,615 A | 8/1991 | Kane |
| 5,049,673 A | 9/1991 | Tsien et al. |
| 5,208,148 A | 5/1993 | Haugland et al. |
| 5,246,867 A | 9/1993 | Lakowicz et al. |
| 5,302,731 A | 4/1994 | Pitner et al. |
| 5,340,716 A | 8/1994 | Ullman et al. |
| 5,380,880 A | 1/1995 | Pitner et al. |
| 5,393,514 A | 2/1995 | Pitner et al. |
| 5,451,343 A | 9/1995 | Neckers et al. |
| 5,622,821 A | 4/1997 | Selvin et al. |
| 5,623,080 A | 4/1997 | Neckers et al. |
| 5,639,615 A | 6/1997 | Selvin et al. |

(Continued)

FOREIGN PATENT DOCUMENTS

| | | |
|---|---|---|
| EP | 0314480 | 5/1989 |
| EP | 0515133 | 11/1992 |
| EP | 0582836 | 2/1994 |
| EP | 1069121 | 1/2001 |

(Continued)

OTHER PUBLICATIONS

U.S. Appl. No. 10/598,371 to Nagano et al.
Reyes, J.G., et al., Biol. Res., 27, pp. 49-56, 1994.
Tsuda, M., et al., Neurosci., 17, pp. 6678-6684, 1997.
Koike, T., et al., J. Am. Chem. Soc., 118, pp. 12696-12703, 1996.
Saibou Kougaku (Cell Technology), 17, pp. 584-595, 1998.
Tanpakushitsu.Kakusan.Kouso (Protein, Nucleic Acid and Enzyme), extra number, 42, pp. 171-176, 1997.
Tetsuji Kametani, Nankodo Co., Ltd., pp. 214-215, 1997.
Handbook of Fluorescent Probes and Research Chemicals, 6th Edition by Richard P. Haugland, pp. 503 and 531-540.

(Continued)

*Primary Examiner*—Taofiq A Solola
(74) *Attorney, Agent, or Firm*—Greenblum & Bernstein, P.L.C.

(57) ABSTRACT

A compound represented by the following general formula (IA) or (IB) or a salt thereof which specifically traps a zinc ion and emits fluorescence, and is useful as a fluorescent probe for zinc:

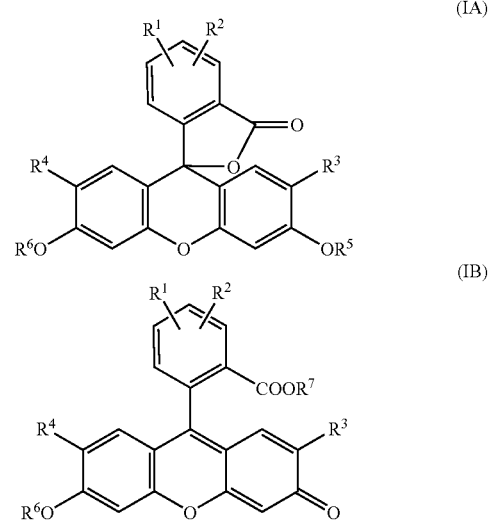

wherein $R^1$ and $R^2$ represent a hydrogen atom or a group represented by the following formula (A):

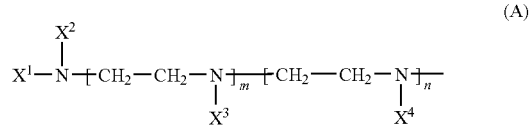

wherein $X^1$ to $X^4$ represent a hydrogen atom, a 2-pyridylmethyl group, a 2-pyridylethyl group, a 2-methyl-6-pyridylmethyl group, or a 2-methyl-6-pyridylethyl group, provided that at least one is the group except a 2-pyridylmethyl group, and m and n represent 0 or 1, provided that they are not simultaneously 0; provided that $R^1$ and $R^2$ are not simultaneously hydrogen atoms; $R^3$ and $R^4$ represent a hydrogen atom or a halogen atom; $R^5$ and $R^6$ represent a hydrogen atom, an alkylcarbonyl group, or an alkylcarbonyloxymethyl group; and $R^7$ represents a hydrogen atom or an alkyl group.

11 Claims, 5 Drawing Sheets

U.S. PATENT DOCUMENTS

| | | | |
|---|---|---|---|
| 5,648,270 | A | 7/1997 | Kuhn et al. |
| 5,656,433 | A | 8/1997 | Selvin et al. |
| 5,800,996 | A | 9/1998 | Lee et al. |
| 5,863,727 | A | 1/1999 | Lee et al. |
| 5,874,590 | A | 2/1999 | Nagano et al. |
| 6,013,802 | A | 1/2000 | Hoyland et al. |
| 6,201,134 | B1 | 3/2001 | Nagano et al. |
| 6,403,625 | B1 | 6/2002 | Nagao et al. |
| 6,441,197 | B1 | 8/2002 | Nagano et al. |
| 6,469,051 | B2 | 10/2002 | Nagano et al. |
| 6,525,088 | B1 | 2/2003 | Nagano et al. |
| 6,569,892 | B2 | 5/2003 | Nagano et al. |
| 6,656,927 | B1 | 12/2003 | Nagano et al. |
| 6,753,156 | B1 | 6/2004 | Mathis et al. |
| 6,756,231 | B1 | 6/2004 | Nagano et al. |
| 6,833,386 | B2 | 12/2004 | Nagano et al. |
| 6,903,226 | B2 | 6/2005 | Nagano et al. |
| 6,936,687 | B1 | 8/2005 | Komoriya et al. |
| 6,972,182 | B1 | 12/2005 | Colyer et al. |
| 2002/0177120 | A1 | 11/2002 | Elliott et al. |
| 2003/0153027 | A1 | 8/2003 | Nagano et al. |
| 2003/0157727 | A1 | 8/2003 | Nagano et al. |
| 2003/0162298 | A1 | 8/2003 | Nagano et al. |
| 2004/0043498 | A1 | 3/2004 | Nagano et al. |
| 2004/0147035 | A1 | 7/2004 | Nagano et al. |
| 2005/0037332 | A1 | 2/2005 | Komatsu et al. |
| 2005/0064308 | A1 | 3/2005 | Nagano et al. |
| 2005/0123478 | A1 | 6/2005 | Nagano et al. |
| 2005/0130314 | A1 | 6/2005 | Nagano et al. |
| 2005/0182253 | A1 | 8/2005 | Yano et al. |
| 2006/0030054 | A1 | 2/2006 | Nagano et al. |

FOREIGN PATENT DOCUMENTS

| | | |
|---|---|---|
| EP | 1260508 | 11/2002 |
| EP | 1260510 | 11/2002 |
| JP | 60-54381 | 3/1985 |
| JP | 6-207112 | 7/1994 |
| JP | 06-211831 | 8/1994 |
| JP | 08-271430 | 10/1996 |
| JP | 9-101262 | 4/1997 |
| JP | 10-88124 | 4/1998 |
| JP | 10-226688 | 8/1998 |
| JP | 5-180773 | 7/1999 |
| JP | 2000-111480 | 4/2000 |
| JP | 2000-239272 | 9/2000 |
| WO | 89/09408 | 10/1989 |
| WO | 96/42016 | 12/1996 |
| WO | 98/15830 | 4/1998 |
| WO | 99/15896 | 4/1999 |
| WO | 99/51586 | 10/1999 |
| WO | 00/00819 | 1/2000 |
| WO | 01/62755 | 8/2001 |
| WO | 01/63265 | 8/2001 |
| WO | 01/64664 | 9/2001 |
| WO | 2004/040296 | 5/2004 |
| WO | 2005024049 | 3/2005 |
| WO | 2005/085811 | 9/2005 |

OTHER PUBLICATIONS

Protective Groups in Organic Synthesis, T. W. Greene, John Wiley & Sons, Inc. pp. v-xxi and 369-405.
English Language Abstract of JP 2000-239272.
Angew. Chem., Int. Ed. (1999), 38(21), pp. 3209-3212.
Anal. Chem. (1998), 70(13), pp. 2446-2453.
Bioorganic & Medicinal Chemistry, vol. 4, No. 6, pp. 901-916, (1996.
Bioorg. Khim. (1995), 21(10), pp. 795-801.
Sci. China, Ser. B: Chem. (1998), 41(5), pp. 549-555.
J. Am. Chem. Soc. (1996), 118, pp. 6514-6515.
Walkup G. K. et al., "A New Cell-Permeable Fluorescent Probe for $Zn^{2+}$", J. Am. Chem. Soc., vol. 122, No. 23, Jun. 14, 2000, pp. 5644-5645.
Bambot, S.B. et al., "Potential Applications of Lifetime-Based, Phase-Modulation Fluorimetry in Bioprocess and Clinical Monitoring", Trends in Biotechnology, vol. 13, No. 3, Mar. 1995, pp. 106-115, XP 004207135.
Hirano T. et al., "Highly Zinc-Selective Fluorescent Sensor Molecules Suitable for Biological Applications", J. Am. Chem. Soc., vol. 122, No. 49, Dec. 13, 2000, pp. 12399-12400.
Sipior, J. et al., "Lifetime-Based Optical Sensing of pH Using Resonance Energy Transfer in Sol-Gel Films", Sensors and Actuators B; vol. 22, No. 3, Dec. 1994, pp. 181-188, XP004011062.
Selvin, P.R. et al., "Luminescence Energy Transfer Using a Terbium Chelate: Improvements on Fluorescence Energy Transfer", Proceedings of the National Academy of Science of USA, National Academy of Science, Washington, DC, US, vol. 91, Oct. 1994, pp. 10024-10028.
Yuan, J. et al., "Functionalization of Fluorescent Lanthanide Complexes and Their Applications to Biotechnology", Bunseki Kagaku—Japan Analyst; vol. 48, No. 12, pp. 1077-1083 (1999), XP002932633.
English Language Abstract of JP 9-101262.
English Language Abstract of JP 10-88124.
English Language Abstract of JP 2000-111480.
Rogers, M. V., Drug Discovery Today, vol. 2, pp. 156-160, 1997.
Selvin, P. R., et al., J. Am. Chem. Soc., vol. 117, pp. 8132-8138, 1995.
Stryer, L., Ann. Rev. Biochem., vol. 47, pp. 819-846, 1978.
Hemmilä, I., et al., Drug Discovery Today, vol. 2, pp. 373-381, 1997.
New Apoptosis Experimental Protocol, 2nd ed., Yodosha, pp. 201-204, 1999.
Selvin, P. R., et al., J. Am. Chem. Soc., vol. 116, pp. 6029-6030, 1994.
J. Burch, "The Inhibition of Horse-Liver Esterase by Rhodamine B," Biochemical Journal, vol. 59, pp. 97-110 (1955).
D.D. Thomas et al., "Flourescence energy transfer in the rapid-diffusion limit," Proceedings of the National Academy of Sciences of the United States of America, vol. 75, No. 12, pp. 5746-5750 (1978).
S.M. Yeh et al., "Characterization of Transferin Metal-Binding Sites by Diffusion-Enhanced Energy Transfer," Biochemistry, 19, pp. 5057-5062 (1980).
R.A. Edwards et al., "Spectroscopic Studies of Cibacron Blue and Congo Red Bound to Dehydrogenases and Kinases. Evaluation of Dyes as Probes of the Dinucleotide Fold," Biochemistry, vol. 18, No. 23, pp. 5197-5204 (1979).
C.F. Meares et al., "Diffusion-Enhanced Energy Transfer Shows Accessibility of Ribonucleic Acid Polymerase Inhibitor Binding Sites," Biochemistry, 20, pp. 610-617 (1981).
T.G. Wensel et al., "Electrostatic Properties of Myoglobin Probed by Diffusion-Enhanced Energy Transfer," Biochemistry, 22, pp. 6247-6254 (1983).
M.M. Federici et al., "Interaction of Cibacron Blue $F_3GA$ with Glutamine Synthetase: Use of the Dye as a Conformational Probe. 1. Studies Using Unfractionated Dye Samples," Biochemistry, 24, pp. 647-660 (1985).
T.G. Wensel et al., "Diffusion-Enhanced Lanthanide Energy-Transfer Study of DNA-Bound Cobalt(III) Bleomycins: Comparisons of Accessibility and Electrostatic Potential with DNA Complexes of Ethidium and Acridine Orange," Biochemistry, 24, pp. 3060-3069 (1985).
B.S. Isaacs et al., "A Domain of Membrane-Bound Coagulation Factor Va Is Located Far from the Phospholipid Surface. A Fluorescence Energy Transfer Measurement," Biochemistry, 25, pp. 4958-5969 (1986).
T.G. Wensel et al., "Study of Biological Macromolecules by Diffusion-Enhanced Lanthanide Energy Transfer," Journal of the Less-Common Metals, 149, pp. 143-160 (1989).
P.R. Selvin et al., "Luminescence Resonance Energy Transfer," Journal of the American Chemical Society, 116, pp. 6029-6030 (1994).
T. Yamamoto et al., "Determination of Electrostatic Potential Around Specific Locations on the Surface of Actin by Diffusion-enhanced Fluorescence Resonance Energy Transfer," Journal of Molecular Biology, 241, pp. 714-731 (1994).

S.C.J. Meskers et al., "Analysis of Delayed Luminescence from Some Quenchers of Tb(DPA)$_3^{3-}$ Emission: Proof for an Energy Transfer Quenching Mechanism," Journal of Alloys and Compounds, 250, pp. 332-335 (1997).

D.D. Root, "In situ Molecular Association of Dystrophin with Actin Revealed by Sensitized Emission Immuno-Resonance Energy Transfer," Proceedings of the National Academy of Sciences of the United States of America, 94, pp. 5685-5690 (1997).

C. Mucignat-Caretta et al., "Building of Two Fluorescent cAMP Analogues to Type I and II Regulatory Subunits of cAMP-Dependent Protein Kinases," Biochimica et Biophysica Acta, 1357, pp. 81-90 (1997).

Y.-W. Park et al., "Homogeneous Proximity Tyrosine Kinase Assays: Scintillation Proximity Assay versus Homogeneous Time-resolved Fluorescence," Analytical Biochemistry, 269, pp. 94-104 (1999).

K. Blomberg et al., "Terbium and Rhodamine as Labels in a Homogeneous Time-resolved Fluorometric Energy Transfer Assay of the β Subunit of Human Chorionic Gonadotropin in Serum," Clinical Chemistry, 45, 855-861 (1999).

L.L. Pearce et al., "Role of Metallothionein in Nitric Oxide Signaling as Revealed by a Green Fluorescent Fusion Protein," Proceedings of the National Academy of Sciences of the United States of America, 97, pp. 477-482 (2000).

M. Koresawa et al., "Development of a Time-Resolved Fluorometric Detection System Using Diffusion-Enhanced Energy Transfer," Analytical Chemistry, 72, pp. 4904-4907 (2000).

English Language Abstract of JP 60-54381.

T. Nagano et al., "Specific Detection Method and Useful Generating System of Singlet Oxygen," Free Radicals in Clinical Medicine, vol. 7, pp. 35-41 (1993).

I. Saito et al., "Methyl-Substituted Poly(vinylnaphthalene) as a Reversible Singlet Oxygen Carrier," J. Am. Chem. Soc., vol. 107, pp. 6329-6334, 1985.

T. W. Greene et al., "Protective Groups in Organic Synthesis," John Wiley & Sons, Inc., pp. v-xxi and 369-405 (1981).

J. Kabatc et al., "Free Radical Polymerization Initiated via Photoinduced Intermolecular Electron Transfer Process: Kinetic Study 3$^1$," Polymer 40(3), pp. 735-745 (1999).

K. Setsukinai et al., "Fluorescence Switching by O-dearylation of 7-aryloxycoumarins. Development of Novel Flourescence Probes to Detect Reactive Oxygen," J. Chem. Soc., Perkin Trans. 2, 12, pp. 2453-2457, (2000).

J.W. Firth et al., "Some Phenoxy-2H-benzo[b]pyrans," J. Chem. Research (S), vol. 2000, No. 7, pp. 308-308 (Jul. 2000).

Anderegg et al., Helvetica Chimica Acta, Vo.. 50, pp. 2330-2333 (1967).

T. Hirano et al., "Highly Zinc-Selective Fluorescent Sensor Molecules Suitable for Biological Applications," Journal of the American Chemical Society, vol. 122, No. 49, pp. 12399-12400 (2000).

R.P. Haugland, "Handbook of Fluorescent probes and Research Products," 9th Edition Supplement, Chapter 20, pp. 805-817 (2002).

G.K. Walkup et al., "A New Cell-Permeable Fluorescent Probe for Zn$^{2+}$," Journal of the American Chemical Society, vol. 122, No. 23, pp. 5644-5645 (2000).

J. Kawakami et al., "Ab initio Molecular Orbital Study of Emission Mechanism of 2,6-Bis(quinolinecarboxy) methylpyridine as Fluorescent Chemosensors for Zinc and Cadmium Ions," Journal of Computer Chemistry, Japan, vol. 2, No. 2, pp. 57-62 (2003).

C.J. Frederickson et al., "A quinoline fluorescence method for visualizing and assaying the histochemically reactive zinc (bouton zinc) in the brain," Journal of Neuroscience Methods, vol. 20, pp. 91-103 (1987).

D. Zalewski et al., "Correlation of apoptosis with change in intracellular labile Zn(II) using Zinquin [(2-methyl-8-*p*-toluenesulphonamido-6-quinolyloxy)acetic acid], a new specific fluorescent probe for Zn(II)," Biochemical Journal, vol. 296, Part 2, pp. 403-408 (1993).

English Language Abstract of JP 10-226688.

L. Lindqvist et al., "Radiationless Transitions in Xanthene Dyes", J. Chem. Phys., vol. 44, pp. 1711-1712 (1966).

Richard P. Haugland, Handbook of Fluorescent Probes and Research Chemicals, Sixth Edition, Chapters 22-24, pp. 503-584 (1996).

Theodora W. Greene, Protective Groups in Organic Synthesis, Chapter 7, pp. 218-287 (1981).

English language Abstract of JP 2000-239272.

English Language Abstract of JP 08-2714430.

Rajendra Nath Sen et al., "The Condensation of Primary Alcohols with Resorcinol and Other Hydroxy Aromatic Compounds", J. Am. Chem. Soc., vol. 47, pp. 1079-1091 (1925), XP002332482.

R. Kurduker et al., "Search for Physiologically Active Compounds", Proc. Indian. Acad. Sci. Sect. A., vol. 57, pp. 280-287 (1963).

A. Minta et al., "Fluorescent Indicators for Cytosolic Calcium Based on Rhodamine and Fluorescein Chromophores", J. Biol. Chem., vol. 264, No. 14, pp. 8171-8178 (1989).

P.K. Grover et al., "Xanthones. Part IV. A New Synthesis of Hydroxyxanthones and Hydroxybenzophenones," J. Chem. Sci. (London), pp. 3982-3985 (1955).

English Language Abstract of JP 06-211831.

William A. Pryor et al., "A Practical Method for Preparing Peroxynitrite Solutions of Low Ionic Strength and Free of Hydrogen Peroxide," Free Radical Biology & Medicine, vol. 18, No. 1, pp. 75-83 (1995).

Stephen L. Hempel et al., "Dihydrofluorescein Diacetate is Superior for Detecting Intracellular Oxidants: Comparison with 2',7'-Dichlorodihydrofluorescein Diacetate, 5(and 6)-Carboxy-2',7'-Dichlorodihydrofluorescein Diacetate, and Dihydrorhodamie 123," Free Radical Biology & Medicine, vol. 27, Nos. 1/2, pp. 146-159 (1999).

Joseph A. Hrabie et al., "New Nitric Oxide-Releasing Zwitterions Derived from Polyamines," J. Org. Chem. vol. 58, pp. 1472-1476 (1993).

English Language Abstract of JP 5-180773.

Newport Green: A Catalog of Molecular Probes, Inc. "Handbook of Fluorescent Probes and Research Chemical, Chapter 22—Section 22.7 Fluorescent Indicators for Zn$^{2+}$ and Other Metals", 6th Edition by Richard P. Haugland, pp. 531-540 (1996).

Toshiaki Hiratsuka, "Tanpakushitsu-Kakusan-Kouso (Protein, Nucleic Acid and Enzyme)", vol. 42, No. 7, pp. 171-176 (1997).

English Language Abstract of JP 2000-239272, published Sep. 5, 2000.

J.G. Reyes et al., Biol. Res., vol. 27, pp. 49-56, 1994.

M. Tsuda et al., The Journal of Neuroscience, vol. 17, No. 17, Sep. 1, 1997, pp. 6678-6684.

T. Koike et al., J. Am. Chem. Soc., vol. 118, 1996, pp. 12696-12703.

Screenshot of Web site of the Pharmaceutical Society of Japan, on Feb. 1, 2003.

Abstract of "The 123rd Annual Congress of the Pharmaceutical Society of Japan" on Mar. 5, 2003 for presentation No. 29[P1]I-219 entitled "Development of Fluorescent Probe Having Low Affinity for Zinc" in the 123rd Annual Congress of the Pharmaceutical Society of Japan held on Mar. 27-29, 2003.

(A) Compound 8

(B) Compound 13

(C) Compound 17

(D) Compound 22

FLUORESCENT PROBE FOR ZINC

TECHNICAL FIELD

The present invention relates to a fluorescent probe for zinc that emits fluorescence by specifically trapping a zinc ion.

BACKGROUND ART

Zinc is an essential metallic element that is present in the human body in the largest amount next to iron. Most zinc ions in cells are strongly coupled to proteins and are involved in the maintenance of structure or in the expression of function of the protein. Various reports have been also made on the physiological role of free zinc ions which are present in the cell in a very small quantity (generally at a level of μM or lower). In particular, zinc ions are considered to be significantly involved in one type of cell death, i.e., apoptosis, and it is reported that zinc ions accelerate senile plaque formation in Alzheimer's disease.

A compound (a fluorescent probe for zinc), which specifically traps a zinc ion to form a complex and emits fluorescence upon the formation of the complex, has been conventionally used to measure zinc ions in tissue. For example, TSQ (Reyes, J. G., et al., Biol. Res., 27, 49, 1994), Zinquin ethyl ester (Tsuda, M. et al., Neurosci., 17, 6678, 1997), Dansylaminoethylcyclen (Koike, T. et al., J. Am. Chem. Soc., 118, 12686, 1996), and Newport Green (a catalog of Molecular Probes, Inc.: "Handbook of Fluorescent Probes and Research Chemicals" 6th Edition by Richard P. Haugland pp. 531-540) have been used practically as fluorescent probes for zinc.

The measurement using TSQ, Zinquin, or Dansylaminoethylcyclen, however, requires the use of a short wavelength excitation light (an excitation wavelength of 367 nm, 368 nm, and 323 nm, respectively). Accordingly, when these fluorescent probes for zinc are used for measurement in living systems, the short wavelength excitation light may cause damages of cells (Saibou Kougaku (Cell Technology), 17, pp. 584-595, 1998). A problem also arises that the measurement may be readily influenced by autofluorescence generated from cell systems, per se (fluorescence emitted by NADH or flavins). Further, Dansylaminoethylcyclen suffers from a disadvantage: When the concentration is determined using the reagent, the fluorescence intensities are vary greatly depending on differences in environment such as solvents, whether a solubility in water or in lipid is extra-, intra-cell or cell membrane; or the like (Tanpakushitsu-Kakusan-Kouso (Protein, Nucleic Acid and Enzyme), extra number, 42, pp. 171-176, 1997). TSQ has a problem that even distribution in the whole cell is difficult due to its high lipophilicity. Newport Green has low affinity for zinc ions and fails to achieve practical measurement sensitivity, although the agent enables measurement with a long wavelength excitation light. Therefore, the development of a fluorescent probe for zinc has been desired that can measure zinc ions with high sensitivity without damaging cells.

The inventors of the present invention conducted various studies to provide a fluorescent probe for zinc with high sensitivity. As a result, they found that a compound having a cyclic amine or a polyamine as a substituent has high specificity with zinc ions, and by trapping zinc ions, the compound forms a complex which emits strong fluorescence with a excitation light in longer wavelength range (Japanese Patent Application No. (Hei) 11-40325). In addition, the inventors further conducted studies and succeeded in providing a fluoresceine derivative by which zinc in the living organism can be measured with very high accuracy and sensitivity (International Publication WO 01/62755). However, this fluoresceine derivative has extremely high affinity for a zinc ion, and this causes a difficulty in accurately measuring zinc ions in a high concentration, although the derivative was excellent in detection of zinc ions in a low concentration. Therefore, it has been desired to provide a means which can accurately measure the concentration of zinc ions in a broader range.

DISCLOSURE OF THE INVENTION

An object of the present invention is to provide a means to accurately measure zinc ions in a broad range from a low concentration to a high concentration. The inventors of the present invention have conducted various studies to achieve the foregoing object. As a result, they found that zinc ions in a high concentration can be accurately measured by modifying the fluoresceine derivative described in International Publication WO 01/62755, and that the concentration of zinc ions over an extremely broad range of the concentration can be accurately measured by combining the novel fluoresceine derivative provided as mentioned above and the fluoresceine derivative described in International Publication WO 01/62755. The present invention was achieved on the basis of these findings.

The present invention thus provides a compound represented by the following general formula (IA) or (IB) or a salt thereof:

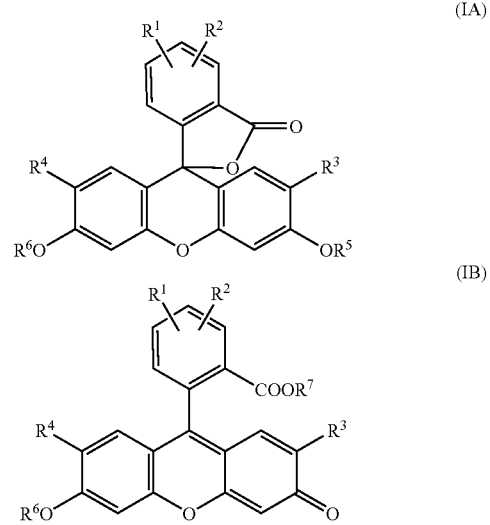

wherein $R^1$ and $R^2$ independently represent a hydrogen atom or a group represented by the following formula (A):

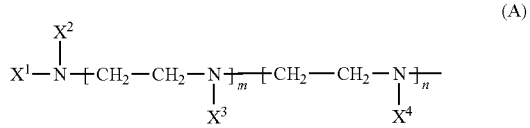

wherein $X^1$, $X^2$, $X^3$, and $X^4$ independently represent a hydrogen atom, a 2-pyridylmethyl group, a 2-pyridylethyl group, a 2-methyl-6-pyridylmethyl group, or a 2-methyl-6-pyridylethyl group, provided that at least one among the groups selected from the group consisting of $X^1$, $X^2$, $X^3$, and $X^4$ represents a group selected from the group consisting of a 2-pyridylethyl group, a 2-methyl-6-pyridylmethyl group, and a 2-methyl-6-pyridylethyl group, and m and n independently represent 0 or 1, provided that m and n do not simultaneously represent 0; provided that $R^1$ and $R^2$ do not simultaneously represent hydrogen atoms; $R^3$ and $R^4$ independently represent a hydrogen atom or a halogen atom; $R^5$ and $R^6$ independently represent a hydrogen atom, an alkylcarbonyl group, or an alkylcarbonyloxymethyl group; and $R^7$ represents a hydrogen atom or an alkyl group.

As a preferred embodiment of the aforementioned invention, provided is a compound represented by the following general formula (IIA) or (IIB) or a salt thereof:

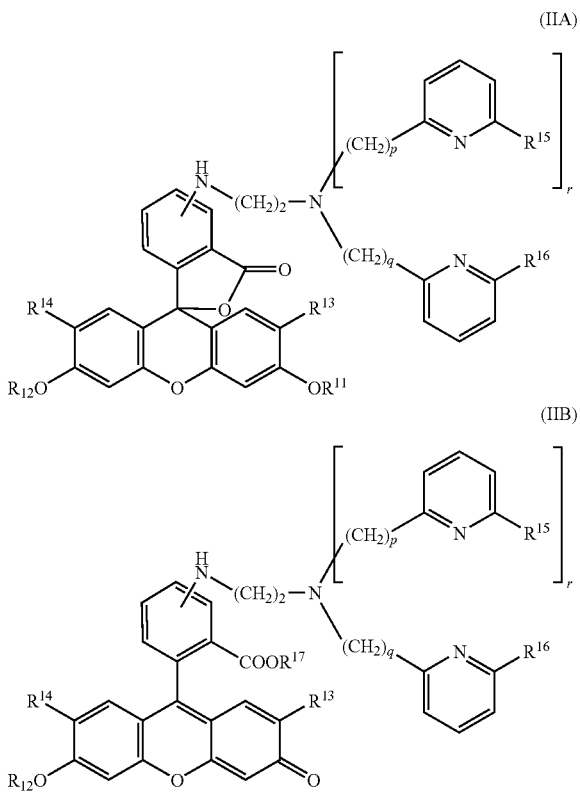

wherein $R^{11}$ and $R^{12}$ independently represent a hydrogen atom, an alkylcarbonyl group, or an alkylcarbonyloxymethyl group; $R^{13}$ and $R^{14}$ independently represent a hydrogen atom or a halogen atom; $R^{15}$ and $R^{16}$ independently represent a hydrogen atom or a methyl group; $R^{17}$ represents a hydrogen atom or an alkyl group; p and q independently represent 1 or 2; and r represents 0 or 1, provided that when r is 1, excluded is the compound wherein $R^{15}$ and $R^{16}$ are simultaneously hydrogen atoms, and p and q are simultaneously 1, and when r is 0, q is 2, and the 2-pyridylalkyl group on the nitrogen is replaced by a hydrogen atom.

According to preferred embodiments of the above invention, provided are the aforementioned compound or a salt thereof wherein $R^{11}$, $R^{12}$, $R^{13}$ and $R^{14}$ are hydrogen atoms; and the aforementioned compound or a salt thereof wherein $R^{17}$ is a hydrogen atom, and according to a further preferred embodiment, provided is the compound or a salt thereof in which the substituted amino group on the benzene ring binds in m-position or p-position relative to the group represented by —$COOR^{17}$.

From another aspect, the present invention provides a fluorescent probe for zinc which comprises a compound represented by the aforementioned general formula (IA), (IB), (IIA) or (IIB), or a salt thereof; and a zinc complex which is formed by a compound represented by the aforementioned general formula (IA), (IB), (IIA) or (IIB), or a salt thereof together with a zinc ion. The fluorescent probe for zinc can be used for measuring zinc ions in tissues or cells.

Further, the present invention provides a method for measuring zinc ions in which a compound represented by the aforementioned general formula (IA), (IB), (IIA), or (IIB) or a salt thereof is used as a fluorescent probe for zinc; a method for measuring zinc ions which comprises the following steps of: (a) reacting a compound represented by the aforementioned general formula (IA), (IB), (IIA), or (IIB) or a salt thereof with zinc ions; and (b) measuring fluorescence intensity of the zinc complex produced in the above step; and a use of a compound represented by the aforementioned general formula (IA), (IB), (IIA), or (IIB) or a salt thereof as a fluorescent probe for zinc.

From a further aspect, the present invention provides a method which comprises the step of measuring zinc ions by using two or more compounds or salts thereof selected from the group consisting of the following (1) to (14) in the following general formula (IIIA) or (IIIB):

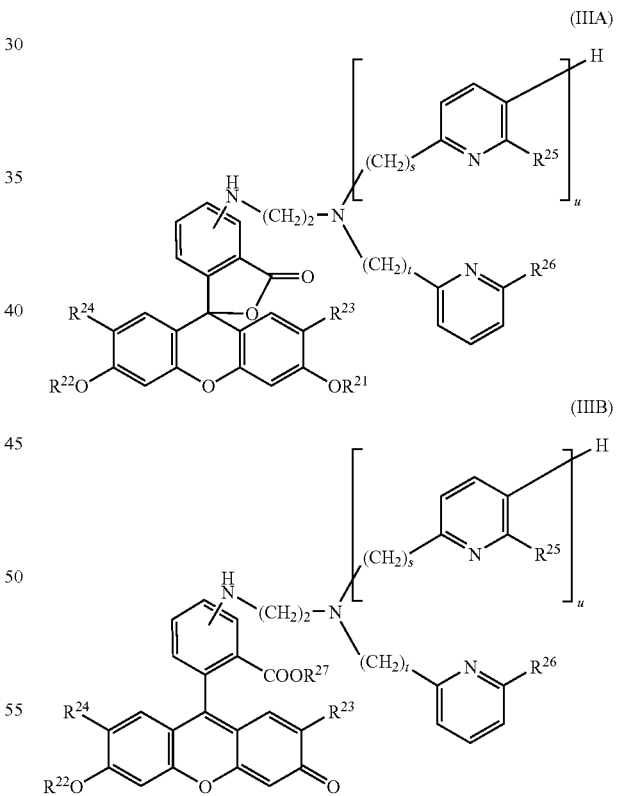

wherein $R^{21}$ and $R^{22}$ independently represent a hydrogen atom, an alkylcarbonyl group, or an alkylcarbonyloxymethyl group; $R^{23}$ and $R^{24}$ independently represent a hydrogen atom or a halogen atom; $R^{25}$ and $R^{26}$ independently represent a hydrogen atom or a methyl group; $R^{27}$ represents a hydrogen atom or an alkyl group; s and t independently represent 1 or 2, and u represents 0 or 1, (1) a compound wherein s and t are 1, u is 1, and $R^{25}$ and $R^{26}$ are hydrogen atoms, or a salt thereof
(2) a compound wherein s and t are 1, u is 1, $R^{25}$ is a hydrogen atom, and $R^{26}$ is a methyl group, or a salt thereof
(3) a compound wherein s and t are 1, u is 1, and $R^{25}$ and $R^{26}$ are methyl groups, or a salt thereof
(4) a compound wherein s is 1, t is 2, u is 1, and $R^{25}$ and $R^{26}$ are hydrogen atoms, or a salt thereof
(5) a compound wherein s is 1, t is 2, u is 1, $R^{25}$ is a hydrogen atom, and $R^{26}$ is a methyl group, or a salt thereof
(6) a compound wherein s is 1, t is 2, u is 1, $R^{25}$ is a methyl group, and $R^{26}$ is a hydrogen atom, or a salt thereof
(7) a compound wherein s is 1, t is 2, u is 1, and $R^{25}$ and $R^{26}$ are methyl groups, or a salt thereof
(8) a compound wherein s and t are 2, u is 1, and $R^{25}$ and $R^{26}$ are hydrogen atoms, or a salt thereof
(9) a compound wherein s and t are 2, u is 1, $R^{25}$ is a hydrogen atom, and $R^{26}$ is a methyl group, or a salt thereof
(10) a compound wherein s and t are 2, u is 1, and $R^{25}$ and $R^{26}$ are methyl groups, or a salt thereof
(11) a compound wherein t is 1, u is 0, and $R^{26}$ is a hydrogen atom, or a salt thereof
(12) a compound wherein t is 1, u is 0, and $R^{26}$ is a methyl group, or a salt thereof
(13) a compound wherein t is 2, u is 0, and $R^{26}$ is a hydrogen atom, or a salt thereof
(14) a compound wherein t is 2, u is 0, and $R^{26}$ is a methyl group, or a salt thereof.

According to a preferred embodiment of the above invention, provided is the aforementioned method wherein $R^{21}$, $R^{22}$, $R^{23}$, $R^{24}$, and $R^{27}$ are hydrogen atoms. According to this method, the selected two or more compounds or salts thereof can form zinc complexes in different ranges of the zinc concentration, and accordingly, zinc ions can be measured in a broad range of the concentration. Further, the present invention provides a kit for measuring zinc ions which comprises two or more compounds or salts thereof selected from the group consisting of the aforementioned compounds or salts thereof (1) to (14).

BEST MODE FOR CARRYING OUT THE INVENTION

Figure 1:
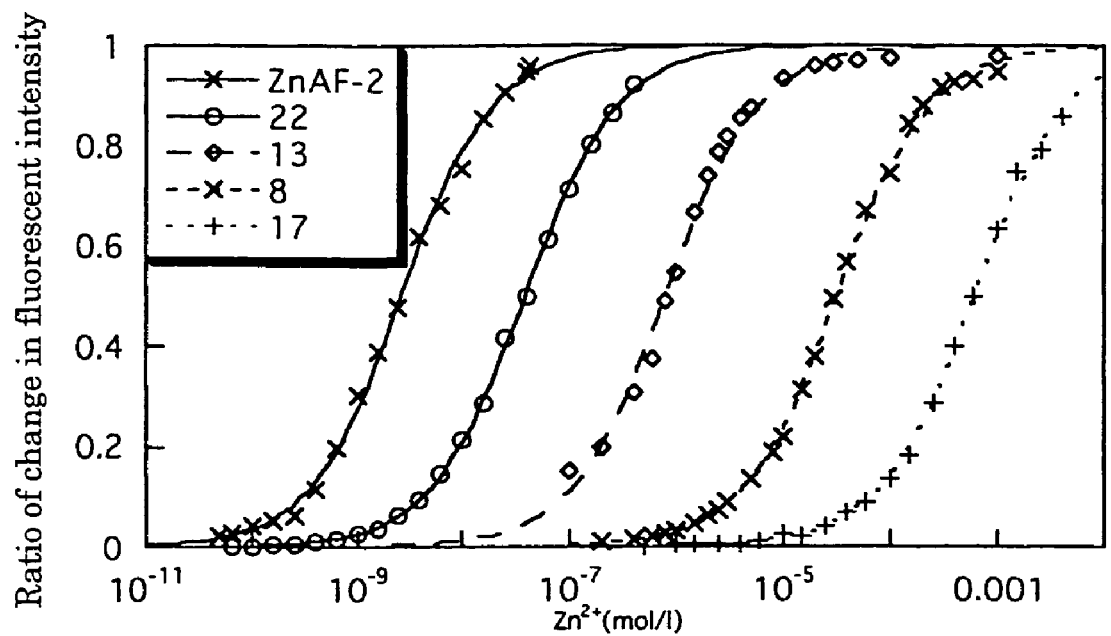
FIG. 1 shows changes in fluorescence intensity of each of the test compounds with relation to changes in the concentration of zinc ions.

"An alkyl group" or an alkyl moiety of a substituent containing the alkyl moiety (for example, an alkylcarbonyl group or an alkylcarbonyloxymethyl group) used in the specification means, for example, a linear, branched, or cyclic alkyl group, or an alkyl group comprising a combination thereof having 1 to 12 carbon atoms, preferably 1 to 6 carbon atoms, and more preferably 1 to 4 carbon atoms. More specifically, a lower alkyl group (an alkyl group having 1 to 6 carbon atoms) is preferred for an alkyl group. Examples of the lower alkyl groups include methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group and the like. When "a halogen atom" is referred to, the term means any of a fluorine atom, a chlorine atom, a bromine atom, or an iodine atom, and preferably means a fluorine atom, a chlorine atom, or a bromine atom.

In the aforementioned general formulas (IA) and (IB), the positions of $R^1$ and $R^2$ substituted on the benzene ring are not particularly limited. When $R^2$ is a hydrogen atom, it is preferred that $R^1$ binds in the meta-position or the para-position relative to the group represented by —$COOR^7$ (or the corresponding carbonyl group when a lactone ring is formed). The position of the substituted amino group on the benzene ring in the general formulas (IIA) and (IIB) is not particularly limited; however, the position is preferably meta-position or para-position relative to the group represented by —$COOR^{17}$, and most preferably para-position relative to the group represented by —$COOR^{17}$.

In the compounds represented by the aforementioned general formulas (IA) and (IB), it is preferred that either of $R^1$ and $R^2$ is a hydrogen atom and the other is a group represented by the formula (A). In the group represented by the formula (A), $X^1$, $X^2$, $X^3$, and $X^4$ independently represent a hydrogen atom, a 2-pyridylmethyl group, a 2-pyridylethyl group, a 2-methyl-6-pyridylmethyl group, or a 2-methyl-6-pyridylethyl group, provided that at least one among the groups selected from the group consisting of $X^1$, $X^2$, $X^3$, and $X^4$ represents a group selected from the group consisting of a 2-pyridylethyl group, a 2-methyl-6-pyridylmethyl group, and a 2-methyl-6-pyridylethyl group. In the compounds represented by the aforementioned general formulas (IA) and (IB), it is preferred that m is 0, n is 1 and $X^4$ is a hydrogen atom, and in said compound, it is preferred that at least one of $X^1$ and $X^2$ is a group selected from the group consisting of 2-pyridylethyl group, a 2-methyl-6-pyridylmethyl group, and a 2-methyl-6-pyridylethyl group. When m is 0, n is 1 and $X^4$ is a hydrogen atom, it is preferred that $X^1$ is a group selected from the group consisting of 2-pyridylethyl group, a 2-methyl-6-pyridylmethyl group, and a 2-methyl-6-pyridylethyl group, and $X^2$ is a group selected from the group consisting of a 2-pyridylmethyl group, a 2-pyridylethyl group, a 2-methyl-6-pyridylmethyl group, and a 2-methyl-6-pyridylethyl group.

$R^5$ and $R^6$ are preferably hydrogen atoms, and for imaging application $R^5$ and $R^6$ are preferably acetyl groups or acetoxymethyl groups. It is preferred that both $R^3$ and $R^4$ are hydrogen atoms or chlorine atoms. $R^7$ is preferably a hydrogen atom.

In the compound represented by the aforementioned general formula (IIA) or (IIB), $R^{11}$ and $R^{12}$ are preferably hydrogen atoms, and for imaging application $R^{11}$ and $R^{12}$ are preferably acetyl groups or acetoxymethyl groups. It is preferred that both $R^{13}$ and $R^{14}$ are both hydrogen atoms or both chlorine atoms at a time, and it is further preferred that both $R^{13}$ and $R^{14}$ are hydrogen atoms. $R^{17}$ is preferably a hydrogen atom. In the compound represented by the general formula (IIA) or (IIB), preferred are the compound wherein p and q are 1, $R^{15}$ is a hydrogen atom and $R^{16}$ is a methyl group; the compound wherein p and q are 1, and $R^{15}$ and $R^{16}$ are methyl groups; the compound wherein p is 1, q is 2, and $R^{15}$ and $R^{16}$ are hydrogen atoms; the compound wherein p is 1, q is 2, $R^{15}$ is a hydrogen atom, and $R^{16}$ is a methyl group; the compound wherein p is 1, q is 2, $R^{15}$ is a methyl group, and $R^{16}$ is a hydrogen atom; the compound wherein p is 1, q is 2, and $R^{15}$ and $R^{16}$ are methyl groups; the compound wherein p and q are 2, and $R^{15}$ and $R^{16}$ are hydrogen atoms; the compound wherein p and q are 2, $R^{15}$ is a hydrogen atom, and $R^{16}$ is a methyl group; and the compound wherein p and q are 2, and $R^{15}$ and $R^{16}$ are methyl groups.

The compounds of the present invention represented by the aforementioned general formula (IA), (IB), (IIA), or (IIB) can exist as acid addition salts or base addition salts. Examples of the acid addition salts include: mineral acid salts such as hydrochloride, sulfate, and nitrate; and organic acid salts such as methanesulfonate, p-toluenesulfonate, oxalate, citrate, and tartrate. Examples of the base addition salts include: metal salts such as sodium salts, potassium salts, calcium salts, and magnesium salts; ammonium salts; and organic amine salts such as triethylamine salts. In addition, salts of amino acids such as glycine may be formed. The compounds or salts thereof according to the present invention may exist as hydrates or solvates, and these substances fall within the scope of the present invention.

The compounds of the present invention represented by the aforementioned general formula (IA), (IB), (IIA), or (IIB) may have one or more asymmetric carbons depending on the types of the substituents. Stereoisomers such as optically active substances based on one or more asymmetric carbons and diastereoisomers based on two or more asymmetric carbons, as well as any mixtures of the stereoisomers, racemates and the like fall within the scope of the present invention. When $R^7$, $R^{17}$, or $R^{27}$ is a hydrogen atom, a carboxyl group may form a lactone, and such structural isomers also fall within the scope of the present invention. A compound represented by the general formula (IA) in which $R^5$ is a hydrogen atom and a compound represented by the general formula (IB) in which $R^7$ is a hydrogen atom fall under tautomers, and a compound represented by the general formula (IIA) in which $R^{11}$ is a hydrogen atom and a compound represented by the general formula (IIB) in which $R^{17}$ is a hydrogen atom fall under tautomers. One of ordinary skill in the art would readily recognize the existence of such tautomers, and therefore, it should be understood that any of these tautomers fall within the scope of the present invention.

Methods for preparing typical compounds among the compounds of the present invention are shown in the following schemes. The preparation methods described in the schemes are more specifically shown in further detail in the examples of the specification. Accordingly, one of ordinary skill in the art can prepare any of the compounds according to the present invention represented by the aforementioned general formulas by suitably choosing starting reaction materials, reaction conditions, reagents and the like based on these explanations, and if necessary, modifying and altering these methods. International Publication WO 01/62755 discloses a method for preparing a fluorescein derivative for measurement of zinc ions, and by referring to said publication, the compounds of the present invention may be readily prepared. All the disclosure in International Publication WO 01/62755 is incorporated herein by reference.

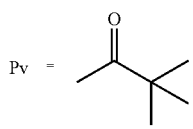

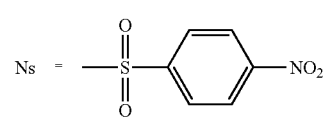

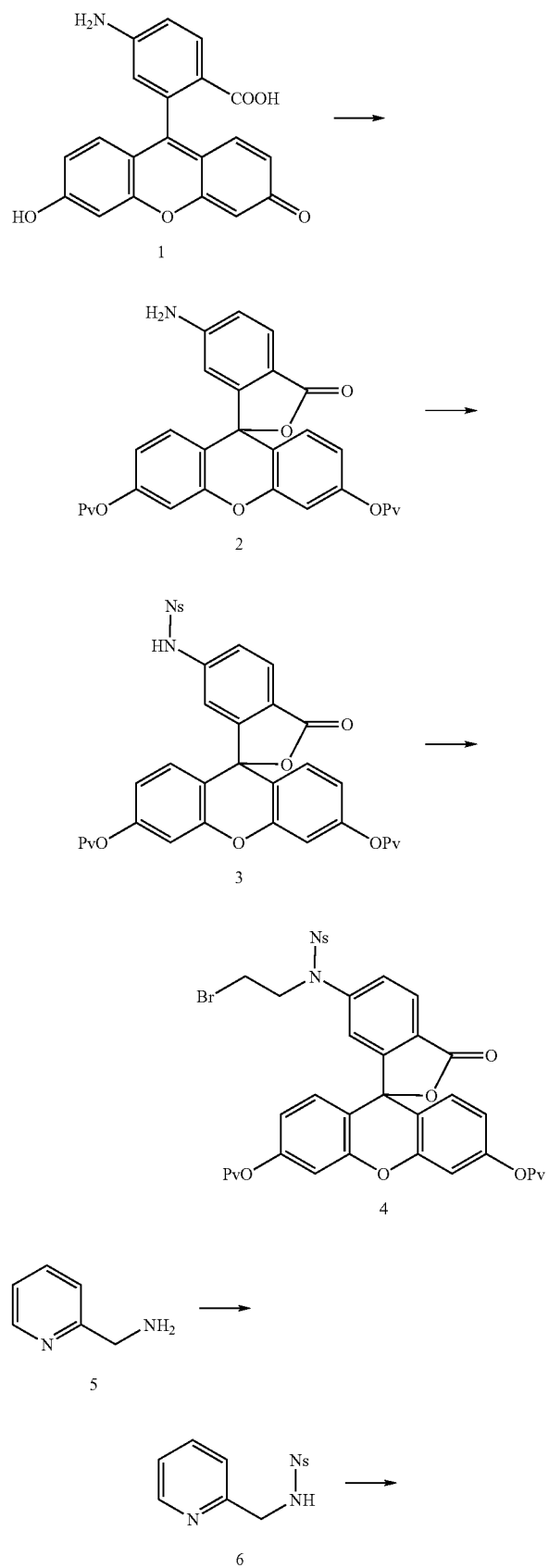

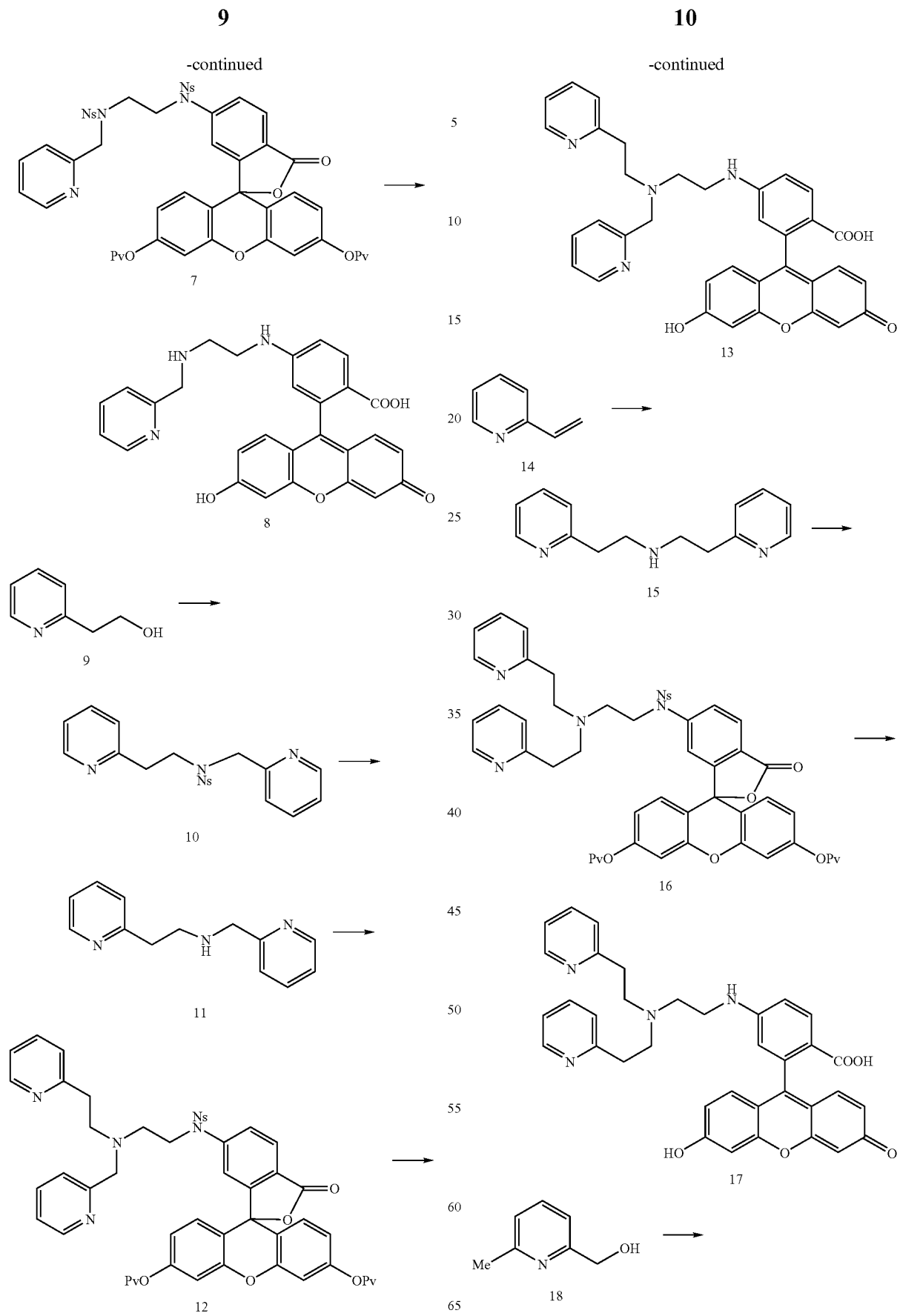

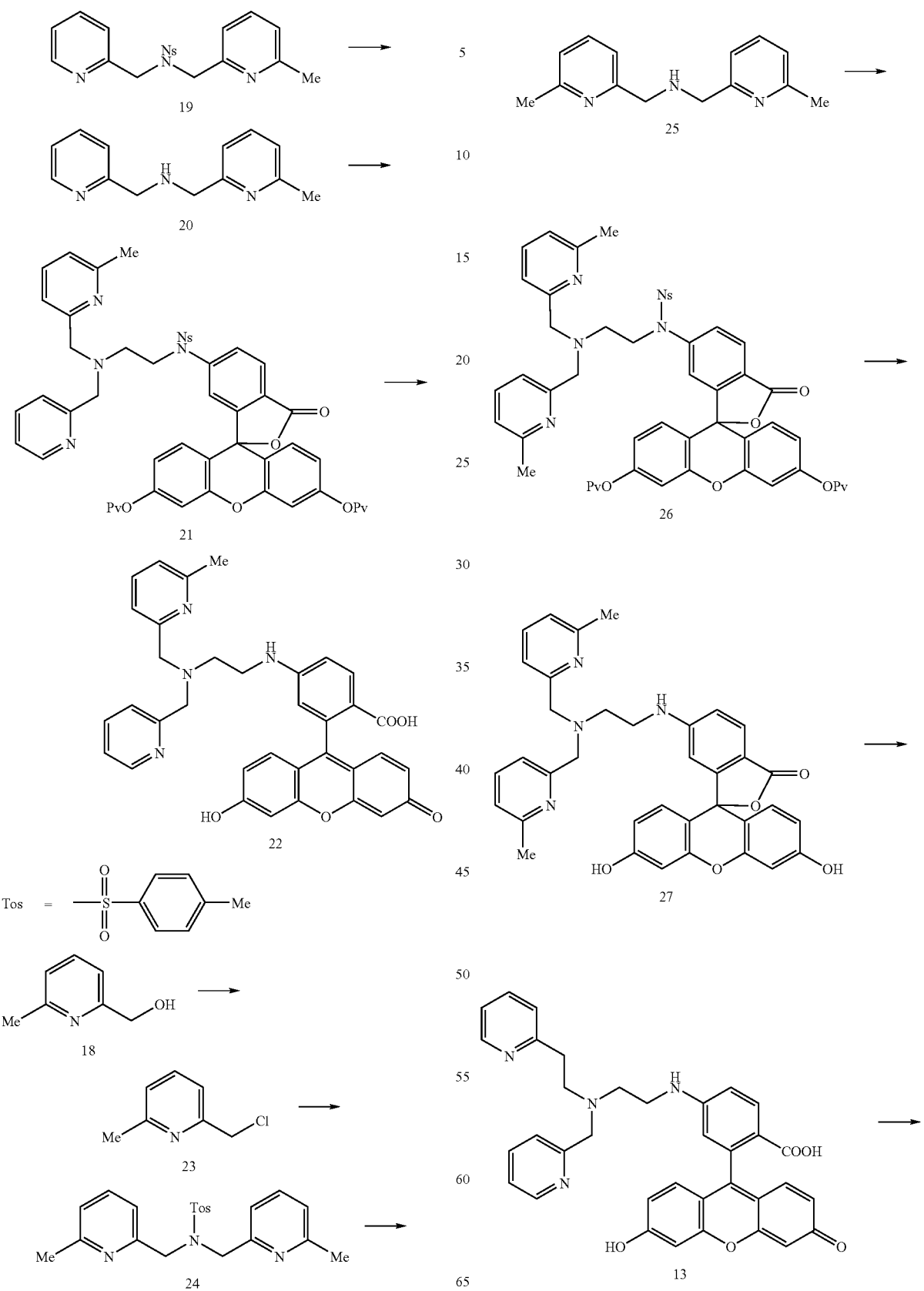

-continued

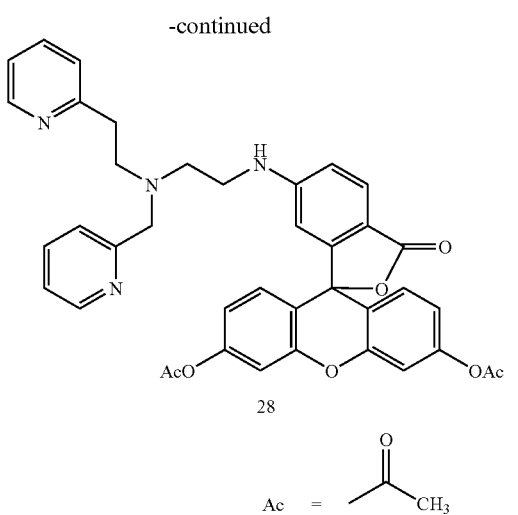

28

Ac = $\underset{\text{CH}_3}{\overset{\text{O}}{\|}}$

The compounds such as 4-aminofluorescein, 5-aminofluorescein, and 6-aminofluorescein, which can be used as starting compounds, can be prepared in accordance with, for example, "Yuuki Gousei Kagaku (Synthetic Organic Chemistry) IX," (Tetsuji Kametani, Nankodo Co., Ltd., p. 215 (1977)). When the amino group is protected when the reaction is carried out, the type of the protective group is not particularly limited. For example, a p-nitrobenzenesulfonic acid group, a trifluoroacetyl group, a trialkylsilyl group and the like can be suitably used. As for the protective group for amino group, reference can be made to, for example, "Protective Groups in Organic Synthesis," (T. W. Greene, John Wiley & Sons, Inc. (1981)) and the like.

The compounds of the present invention represented by the aforementioned general formula (IA), (IB), (IIA), or (IIB) or salts thereof are useful as fluorescent probes for zinc. While the compounds of the present invention represented by the aforementioned general formula (I) or (II) or salts thereof, per se, do not have the property of emitting strong fluorescence, they come to emit strong fluorescence after the formation of zinc complexes by trapping zinc ions. The above compounds or salts thereof are featured that they can specifically trap zinc ions and form the complexes very rapidly. In addition, the formed zinc complexes are featured to emit strong fluorescence under a long wavelength excitation light which does not cause any damage to living tissues or cells. Accordingly, the compounds of the present invention represented by the aforementioned general formula (IA), (IB), (IIA), or (IIB) or salts thereof are very useful as fluorescent probes for zinc for measurement of zinc ions in living cells or living tissues under a physiological condition. In addition, the compounds of the present invention represented by the aforementioned general formula (IA), (IB), (IIA), or (IIB) or salts thereof are featured that they can form zinc complexes dependent on the zinc concentration in the range of high zinc concentrations, and accordingly, they can suitably be used for measurement of a zinc concentration in samples containing zinc ions at a high concentration. The term "measurement" used in the specification should be construed in its broadest sense, including quantitative and qualitative measurement.

The method for using the fluorescent probe for zinc according to the present invention is not particularly limited, and the probe can be used in the same manner as conventional zinc probes. In general, a substance selected from the group consisting of the compounds represented by the aforementioned general formula (I) and salts thereof is dissolved in an aqueous medium such as physiological saline or a buffered solution, a mixture of the aqueous medium and a water-miscible organic solvent such as ethanol, acetone, ethylene glycol, dimethylsulfoxide, and dimethylformamide or the like, then the resultant solution is added to a suitable buffered solution containing cells or tissues, and a fluorescence spectrum can be measured. The fluorescent probe for zinc according to the present invention may be combined with a suitable additive to use in the form of a composition. For example, the fluorescent probe for zinc can be combined with additives such as a buffering agent, a solubilizing agent, and a pH modifier.

The method for measuring zinc ions which is the second embodiment provided by the present invention comprises the step of measuring zinc ions by using two or more compounds or salts thereof selected from the group consisting of (1) to (14) in the aforementioned general formula (IIIA) or (IIIB):

(1) a compound wherein s and t are 1, u is 1, and $R^{25}$ and $R^{26}$ are hydrogen atoms, or a salt thereof
(2) a compound wherein s and t are 1, u is 1, $R^{25}$ is a hydrogen atom, and $R^{26}$ is a methyl group, or a salt thereof
(3) a compound wherein s and t is 1, u is 1, and $R^{25}$ and $R^{26}$ are methyl groups, or a salt thereof
(4) a compound wherein s is 1, t is 2, u is 1, and $R^{25}$ and $R^{26}$ are hydrogen atoms, or a salt thereof
(5) a compound wherein s is 1, t is 2, u is 1, $R^{25}$ is a hydrogen atom, and $R^{26}$ is a methyl group, or a salt thereof
(6) a compound wherein s is 1, t is 2, u is 1, $R^{25}$ is a methyl group, and $R^{26}$ is a hydrogen atom, or a salt thereof
(7) a compound wherein s is 1, t is 2, u is 1, and $R^{25}$ and $R^{26}$ are methyl groups, or a salt thereof
(8) a compound wherein s and t are 2, u is 1, and $R^{25}$ and $R^{26}$ are hydrogen atoms, or a salt thereof
(9) a compound wherein s and t are 2, u is 1, $R^{25}$ is a hydrogen atom, and $R^{26}$ is a methyl group, or a salt thereof
(10) a compound wherein s and t are 2, u is 1, and $R^{25}$ and $R^{26}$ are methyl groups, or a salt thereof
(11) a compound wherein t is 1, u is 0, and $R^{26}$ is a hydrogen atom, or a salt thereof
(12) a compound wherein t is 1, u is 0, and $R^{26}$ is a methyl group, or a salt thereof
(13) a compound wherein t is 2, u is 0, and $R^{26}$ is a hydrogen atom, or a salt thereof
(14) a compound wherein t is 2, u is 0, and $R^{26}$ is a methyl group, or a salt thereof.

In the general formula (IIIA) or (IIIB), $R^{21}$ through $R^{27}$ have the same meanings as $R^{11}$ through $R^{17}$ in the explanation about the general formula (IIA) or (IIB). It is preferred that both $R^{21}$ and $R^{22}$ are hydrogen atoms, and for imaging application it is preferred that $R^{21}$ and $R^{22}$ are acetyl groups or acetoxymethyl groups. It is preferred that both $R^{23}$ and $R^{24}$ are both hydrogen atoms or both chlorine atoms at a time, and it is further preferred that both $R^{23}$ and $R^{24}$ are hydrogen atoms. It is preferred that $R^{27}$ is a hydrogen atom. Two or more compounds or salts thereof selected from the group consisting of the aforementioned compounds or salts thereof (1) to (14) can form zinc complexes in different ranges of the zinc concentration, and accordingly, zinc ions can be accurately measured in a broad range of concentration by using these two or more compounds or salts thereof in combination. For example, it is preferred that three or more compounds or salts thereof selected from the group consisting of the aforementioned compounds or salts thereof (1) to (14) are used, and more preferably, four or more compounds or salts thereof can be used. It is preferred that at least one in the selected two or more compounds is a compound selected from the compounds other than the aforementioned (1) to (11).

When this method is carried out, the compound or a salt thereof can suitably be selected depending on the concentration of zinc ions which is the subject of measurement. For example, two or more compounds or salts thereof can be selected according to the method which is specifically described in the examples of the specification with reference to the graph of FIG. 1. Compounds 8, 13, 17, and 22 shown in the graph of FIG. 1 are compounds in which $R^{21}$, $R^{22}$, $R^{23}$, $R^{24}$, and $R^{27}$ are hydrogen atoms in the aforementioned (11), (4), (8), and (2), respectively, and zinc ions in the concentration of from $10^{-8}$ to $10^{-3}$ mol/L can be accurately measured with these four compounds. As mentioned above, the selection of the compounds is preferably made by first measuring the changes in fluorescence intensity of each of the compounds versus the changes in the concentration of zinc ions, and then selecting two compounds so that said compounds give a value of 0.5 as the ratio of fluorescence intensity change (fluorescence intensity in a zinc ion concentration/maximum fluorescence intensity) at ten times or more different zinc ion concentrations.

Alternatively, when the aforementioned method is carried out, one or more other reagents used for the measurement of zinc ion concentration can be used in combination. For example, in the graph of FIG. 1, zinc ions in the concentration of $10^{-9}$ to $10^{-3}$ mol/L can be accurately measured by using the aforementioned four compounds in combination with ZnAF-2 which is a known compound (Compound 12 in International Publication WO 01/62755). In addition, a kit for measuring zinc ions which comprises a combination of two or more compounds or salts thereof selected from the group consisting of the aforementioned compounds or salts thereof (1) to (14) also falls within the present invention. In the kit, one or more other reagents used for measurement of the zinc ion concentration may be used in combination.

EXAMPLES

The present invention will be more specifically explained with reference to the following examples. However, the scope of the present invention is not limited to these examples. The compound numbers in the examples correspond to those used in the above schemes.

Example 1

Synthesis of Compound 8

Cesium carbonate (7.9 g, 24 mmol) was added to a solution of 5-aminofluorescein (1) (4.0 g, 12 mmol) dissolved in 80 ml of dimethylformamide. Subsequently, pivalic anhydride (4.9 ml, 24 mmol) was added to this solution, and the mixture was stirred at room temperature for 1 hour. The reaction solution was filtered using a Kiriyama funnel, dimethylformamide was evaporated under reduced pressure, and then purification was carried out by column chromatography on silica gel to obtain Compound 2 (5.9 g). White solid. Yield 100%.

$^1$H-NMR (CDCl$_3$, 300 MHz): 7.77 (d, 1H, J=8.3), 7.01 (d, 2H, J=2.2), 6.95 (d, 2H, J=8.6), 6.80-6.75 (m, 3H), 6.22 (d, 1H, J=1.8), 4.21 (s, 2H), 1.36 (s, 18H) MASS (FAB): 516 (M$^+$+1)

Compound 2 (5.9 g, 12 mmol) was dissolved in 100 ml of methylene chloride, and pyridine (3.5 ml, 46 mmol) was added to the solution. Subsequently, 4-nitrobenzenesulfonyl chloride (7.7 g, 35 mmol) was added, and then the mixture was stirred at room temperature for 6 hours. After 300 ml of methylene chloride was added, the mixture was washed with water and saturated saline, and dried over sodium sulfate. Methylene chloride was evaporated under reduced pressure, and then purification was carried out by column chromatography on silica gel to obtain Compound 3 (5.5 g). White solid. Yield 69%.

$^1$H-NMR (CDCl$_3$, 300 MHz): 8.20 (d, 2H, J=9.0), 7.88 (d, 1H, J=8.2), 7.81 (d, 2H, J=9.0), 7.29-7.26 (m, 1H), 7.05 (d, 2H, J=2.0), 6.83 (d, 1H, J=1.5), 6.74 (dd, 2H, J=8.7, 2.1), 6.68 (d, 2H, J=8.7), 1.38 (s, 18H) MASS (FAB): 701 (M$^+$+1)

Potassium carbonate (3.0 g, 21 mmol) and 1,2-dibromoethane (15 ml, 0.17 mol) were added to a solution of Compound 3 (3.0 g, 4.3 mmol) dissolved in 300 ml of acetonitrile, and the mixture was stirred at 100° C. for 20 hours. Acetonitrile was evaporated under reduced pressure, and the residue was suspended in 500 ml of water. After the suspension was extracted with methylene chloride, the extract was washed with saturated saline, and then dried over sodium sulfate. Methylene chloride was evaporated under reduced pressure, and then purification was carried out by column chromatography on silica gel to obtain Compound 4 (2.9 g). White solid. Yield 84%.

$^1$H-NMR (CDCl$_3$, 300 MHz): 8.12-8.09 (m, 3H), 7.71 (dd, 1H, J=8.2, 1.8), 7.56 (d, 2H, J=9.0), 7.02 (d, 2H, J=2.2), 6.86 (dd, 2H, J=8.6, 2.2), 6.43 (d, 1H, J=1.8), 3.85 (t, 2H, J=6.6), 3.40 (t, 2H, J=6.6), 1.38 (s, 18H) MASS (FAB): 807, 809 (M$^+$+1)

A solution of 4-nitrobenzenesulfonyl chloride (7.2 g, 33 mmol) dissolved in 40 ml of methylene chloride was added dropwise over 30 minutes to a solution of 2-aminomethylpyridine (5) (3 ml, 29 mmol) and pyridine (6 ml, 74 mmol) dissolved in 60 ml of methylene chloride. Following the dropwise addition, the mixture was stirred at room temperature for 1 hour, and then the reaction solution was washed with 2 M aqueous sodium carbonate. The solution was washed with saturated saline, and then dried over sodium sulfate. Methylene chloride was evaporated under reduced pressure, and then purification was carried out by column chromatography on silica gel to obtain Compound 6 (5.4 g). White solid. Yield 64%.

$^1$H-NMR (CDCl$_3$, 300 MHz): 8.44-8.42 (m, 1H), 8.27 (d, 2H, J=8.7), 8.03 (d, 2H, J=8.7), 7.65-7.59 (m, 1H), 7.19-7.13 (m, 2H), 6.25 (s, 1H), 4.34 (s, 2H) MASS (EI): 293 (M$^+$)

Compound 6 (0.15 g, 0.51 mmol) and potassium carbonate (70 mg, 0.51 mmol) were added to a solution of Compound 4 (0.30 g, 0.37 mmol) dissolved in 20 ml of acetonitrile, and the mixture was stirred at 100° C. for 2 hours. After acetonitrile was evaporated under reduced pressure, the residue was dissolved in 2 M aqueous sodium carbonate, and extracted with methylene chloride. The extract was washed with saturated saline, and then dried over sodium sulfate. Methylene chloride was evaporated under reduced pressure, and then purification was carried out by column chromatography on silica gel to obtain Compound 7 (0.12 g). Yellow solid. Yield 31%.

$^1$H-NMR (CDCl$_3$, 300M Hz): 8.24 (d, 2H, J=8.8), 8.10 (d, 2H, J=8.8), 8.07 (d, 1H, J=8.4), 8.03-8.01 (m, 1H), 7.80 (d, 2H, J=8.8), 7.65-7.57 (m, 2H), 7.50 (d, 2H, J=8.8), 7.24 (d, 1H, J=7.7), 7.13-7.08 (m, 1H), 6.97 (d, 2H, J=1.5), 6.82-6.80 (m, 4H), 6.63 (d, 1H, J=1.5), 4.36 (s, 2H), 3.66 (t, 2H, J=7.1), 3.43 (t, 2H, J=7.1), 1.38 (s, 18H) MASS (FAB): 1020 (M$^+$+1)

Potassium carbonate (80 mg, 0.58 mmol) and thiophenol (0.1 ml, 1.0 mmol) were added to a solution of Compound 7 (0.11 g, 0.11 mmol) dissolved in 10 ml of dimethylformamide, and the mixture was stirred at room temperature for 5 hours. A solution of potassium hydroxide (200 mg, 3.4 mmol) dissolved in 1 ml of MeOH and 1 ml of water was added, and the mixture was stirred at room temperature for 2 hours. After the solvent was evaporated under reduced pressure, the residue was dissolved in 2 M hydrochloric acid. The solution was washed with diethyl ether, and then 2 M hydrochloric acid was evaporated under reduced pressure. The residue was purified by ODS column chromatography and reversed phase HPLC to obtain Compound 8 (44 mg) as the 3TFA salt. Brown solid. Yield 48%.

$^1$H-NMR (CDCl$_3$, 300M Hz): 8.39-8.37 (m, 1H), 7.74 (d, 1H, J=8.6), 7.74-7.68 (m, 1H), 7.29-7.24 (m, 2H), 6.86-6.79 (m, 3H), 6.74 (d, 2H, J=2.2), 6.60 (dd, 2H, J=8.8, 2.2), 6.28 (d, 1H, J=2.0), 4.25 (s, 2H), 3.45 (t, 2H, J=6.2), 3.14 (t, 2H, J=6.2) MASS (FAB): 482 (M$^+$+1)

Example 2

Synthesis of Compound 13

2-Pyridineethanol (9) (0.5 ml, 4.4 mol), azodicarboxylic acid ester (40% toluene solution) (2.5 ml, 5.2 mmol), and triphenylphosphine (1.25 g, 4.8 mmol) were added to a solution of Compound 6 (1 g, 3.4 mmol) dissolved in 80 ml of benzene, and the mixture was stirred at room temperature for 3 hours. After benzene was evaporated under reduced pressure, the residue was dissolved in 2 M aqueous sodium carbonate, and extracted with methylene chloride. The extract was washed with saturated saline, and then dried over sodium sulfate. After methylene chloride was evaporated under reduced pressure, purification was carried out by column chromatography on silica gel to obtain Compound 10 (0.95 g). Yellow oil. Yield 70%.

$^1$H-NMR (CDCl$_3$, 300 MHz): 8.43-8.40 (m, 2H, J=8.6), 8.26 (d, 2H, J=8.6), 7.68-7.62 (m, 1H), 7.57-7.51 (m, 1H), 7.38 (d, 1H, J=7.9), 7.20-7.16 (m, 1H), 7.11-7.09 (m, 1H), 7.06 (d, 1H, J=7.7), 4.58 (s, 2H), 3.74 (t, 2H, J=7.3), 3.00 (t, 2H, J=7.3) MASS (FAB): 399 (M$^+$+1)

Potassium carbonate (0.99 g, 7.2 mmol) and thiophenol (0.49 ml, 4.8 mmol) were added to a solution of Compound 10 (0.95 g, 2.4 mmol) dissolved in 50 ml of dimethylformamide, and the mixture was stirred at room temperature for 10 hours. After dimethylformamide was evaporated under reduced pressure, the residue was dissolved in 2 M aqueous sodium carbonate, and extracted with methylene chloride. The extract was washed with saturated saline, and then dried over sodium sulfate. After methylene chloride was evaporated under reduced pressure, purification was carried out by column chromatography on silica gel to obtain Compound 11 (0.37 g). Yellow oil. Yield 73%.

$^1$H-NMR (CDCl$_3$, 300 MHz):

8.54-8.53 (m, 2H), 7.65-7.56 (m, 2H), 7.30 (d, 1H, J=7.7), 7.20-7.09 (m, 3H), 3.96 (s, 2H), 3.12-3.00 (m, 4H), 2.07 (br, 1H) MASS (FAB): 214 (M$^+$+1)

Compound 4 (0.20 g, 0.25 mmol) was suspended in 50 ml of acetonitrile, and added with potassium iodide (0.10 g, 0.60 mmol), potassium carbonate (0.10 g, 0.72 mmol) and Compound 11 (0.20 g, 0.94 mmol), and the mixture was refluxed for 14 hours. After acetonitrile was evaporated under reduced pressure, the residue was dissolved in 2 N aqueous sodium carbonate, and extracted with methylene chloride. The methylene chloride layer was washed with saturated saline, and then dried over sodium sulfate. Methylene chloride was evaporated under reduced pressure, and purification was carried out by column chromatography on silica gel to obtain Compound 12 (38 mg). Yellow solid. Yield 16%.

$^1$H-NMR (CDCl$_3$, 300 MHz): 8.41-8.40 (m, 1H), 8.36-8.34 (m, 1H), 8.08 (d, 2H, J=8.6), 8.00 (d, 1H, J=8.2), 7.58-7.50 (m, 5H), 7.14-7.03 (m, 4H), 6.96 (d, 2H, J=2.2), 6.68 (d, 2H, J=8.6), 6.58 (d, 1H, J=1.5), 3.67 (s, 2H), 3.57 (t, 2H, J=6.6), 2.83-2.76 (m, 4H), 2.66 (t, 2H, J=6.6), 1.31 (s, 18H) MASS (FAB): 940 (M$^+$+1)

Compound 13 (18 mg) was obtained as a 4TFA salt from Compound 12 (38 mg, 40 μmol) in the same manner as that of the synthesis of Compound 8. Brown solid. Yield 43%.

$^1$H-NMR (CDCl$_3$, 300 MHz): 8.33-8.30 (m, 2H), 7.95-7.89 (m, 1H), 7.86-7.80 (m, 1H), 7.65 (d, 1H, J=8.6), 7.43-7.32 (m, 4H), 6.77 (dd, 1H, J=8.6, 2.0), 6.68-6.65 (m, 4H), 6.53 (dd, 2H, J=8.8, 2.4), 6.16 (d, 1H, J=2.4), 4.41 (s, 2H), 3.45-3.41 (m, 4H), 3.24-3.12 (m, 4H) MASS (FAB): 587 (M$^+$+1)

Example 3

Synthesis of Compound 17

2-Aminoethylpyridine (0.56 ml, 4.6 mmol) and glacial acetic acid (0.27 ml, 4.6 mmol) were added to a solution of 2-vinylpyridine (14) (0.5 ml, 4.6 mmol) dissolved in 50 ml of methanol, and the mixture was refluxed under argon for 24 hours. The mixture was cooled to room temperature, then poured into ice water, and neutralized with 2 M aqueous sodium hydroxide. The mixture was extracted with methylene chloride, and the extract was dried over magnesium sulfate. Methylene chloride was evaporated under reduced pressure, and purification was carried out by column chromatography on silica gel to obtain Compound 15 (0.27 g). Yellow oil. Yield 25%.

$^1$H-NMR (CDCl$_3$, 300 MHz): 8.50 (d, 2H, J=4.0), 7.57 (td, 2H, J=7.7, 1.8), 7.16-7.08 (m, 4H), 3.08-3.03 (m, 4H), 2.99-2.94 (m, 4H), 1.96 (br, 1H) MASS (EI): 227 (M$^+$)

Compound 16 (25 mg) was obtained from Compound 4 (0.10 g, 0.12 mmol) and Compound 15 (60 mg, 0.26 mmol) in the same manner as in the synthesis of Compound 12. Yellow solid. Yield 21%.

$^1$H-NMR (CDCl$_3$, 300 MHz): 8.36-8.34 (m, 2H), 8.09 (d, 2H, J=8.6), 8.01 (d, 1H, J=8.2), 7.55-7.50 (m, 4H), 7.09-7.05 (m, 2H), 7.01-6.98 (m, 2H), 6.94 (d, 2H, J=1.1), 6.76-6.75 (m, 4H), 6.64 (d, 1H, J=1.5), 3.45 (t, 2H, J=7.0), 2.80-2.76 (m, 4H), 2.69-2.64 (m, 4H), 2.60 (t, 2H, J=7.0) MASS (FAB): 954 (M$^+$+1)

Compound 17 (12 mg) was obtained as a 4TFA salt from Compound 16 (25 mg, 26 μmol) in the same manner as in the synthesis of Compound 8. Brown solid. Yield 21%.

$^1$H-NMR (CDCl$_3$, 300 MHz): 8.09-8.07 (m, 2H), 7.87-7.81 (m, 2H), 7.76 (d, 1H, J=8.6), 7.38 (d, 2H, J=7.9), 7.31-7.27 (m, 2H), 6.88 (dd, 1H, J=8.6, 2.2), 6.75 (d, 2H, J=8.8), 6.73 (d, 2H, J=2.4), 6.61 (dd, 2H, J=8.8, 2.4), 3.71-3.62 (m, 6H), 3.48 (t, 2H, J=5.7), 3.23 (t, 4H, J=6.4) MASS (FAB): 601 (M$^+$+1)

Example 4

Synthesis of Compound 22

Compound 19 (2.4 g) was obtained from Compound 6 (2.0 g, 6.8 mmol) and 6-methyl-2-pyridinemethanol (18) (1.1 g, 8.8 mmol) in the same manner as in the synthesis of Compound 10. Yellow oil. Yield 88%.

$^1$H-NMR (CDCl$_3$, 300 MHz): 8.39-8.38 (m, 1H), 8.23 (d, 2H, J=8.8), 7.98 (d, 2H, J=8.8), 7.67-7.61 (m, 1H), 7.51-7.45 (m, 1H), 7.39 (d, 1H, J=7.7), 7.17-7.13 (m, 1H), 7.09-7.07 (m, 1H), 6.98-6.95 (m, 1H), 4.68 (s, 2H), 4.63 (s, 2H), 2.30 (s, 3H) MASS (EI): 398 (M$^+$)

Compound 20 (0.78 g) was obtained from Compound 19 (2.4 g, 6.0 mmol) in the same manner as that of the synthesis of Compound 11. Yellow oil. Yield 61%.

$^1$H-NMR (CDCl$_3$, 300 MHz): 8.55 (m, 1H), 7.64 (td, 1H, J=7.5, 1.9), 7.53 (t, 1H, J=7.7), 7.37 (d, 1H, J=7.5), 7.15 (d,

1H, J=7.7), 7.15-7.14 (m, 1H), 7.01 (d, 1H, J=7.7), 3.99 (s, 2H), 3.94 (s, 2H), 2.54 (s, 3H) MASS (FAB): 214 (M$^+$+1)

Compound 21 (0.18 g) was obtained from Compound 4 (0.45 g, 0.56 mmol) and Compound 20 (0.24 g, 1.1 mmol) in the same manner as that of the synthesis of Compound 12. Yellow solid. Yield 35%.

$^1$H-NMR (CDCl$_3$, 300 MHz): 8.43-8.41 (m, 1H), 8.06 (d, 2H, J=8.8), 7.96 (d, 1H, J=8.6), 7.64-7.58 (m, 1H), 7.53-7.48 (m, 2H), 7.51 (d, 2H, J=8.8), 7.35-7.32 (m, 1H), 7.16-7.12 (m, 2H), 7.03-6.99 (m, 1H), 7.00 (d, 2H, J=2.2), 6.76 (dd, 2H, J=8.6, 2.2), 6.62 (d, 2H, J=8.6), 6.46 (d, 1H, J=1.3), 3.69-3.65 (m, 6H,), 2.67 (t, 2H, J=6.2), 2.48 (s, 3H), 1.37 (s, 18H) MASS (FAB): 940 (M$^+$+1)

Compound 22 (76 mg) was obtained as a 4TFA salt from Compound 21 (0.18 g, 0.19 mmol) in the same manner as that of the synthesis of Compound 8. Brown solid. Yield 38%.

$^1$H-NMR (CD$_3$OD, 300 MHz): 8.47-8.45 (m, 1H), 7.95-7.84 (m, 2H), 7.65 (d, 1H, J=8.6), 7.46-7.38 (m, 4H), 6.74 (dd, 1H, J=8.6, 2.0), 6.68 (d, 2H, J=2.4,), 6.65 (d, 2H, J=8.8), 6.56 (dd, 2H, J=8.8, 2.4), 6.07 (d, 1H, J=2.0), 4.32 (s, 2H), 4.28 (s, 2H), 3.30-3.25 (m, 2H), 3.08 (t, 2H, J=5.9), 2.55 (s, 3H) MASS (FAB): 587 (M$^+$+1)

Example 5

Synthesis of Compound 27

Thionyl chloride (12 ml, 0.17 mol) was added dropwise to a solution of 6-methyl-2-pyridinemethanol (18) (4.0 g, 33 mmol) dissolved in 150 ml of methylene chloride. After the dropwise addition was completed, the mixture was refluxed at 45° C. for 1 hour. After methylene chloride was evaporated under reduced pressure, the residue was dissolved in 2 M aqueous sodium carbonate, and extracted with methylene chloride. The methylene chloride layer was washed with saturated saline, and then dried over potassium sulfate. Methylene chloride was evaporated under reduced pressure to obtain Compound 23 (4.5 g). Colorless oil. Yield 97%.

$^1$H-NMR (CDCl$_3$, 300 MHz): 7.60 (t, 1H, J=7.7), 7.28 (d, 1H, J=7.7), 7.09 (d, 1H, J=7.7), 4.64 (s, 2H), 2.56 (s, 3H) MASS (EI): 141 (M$^+$)

p-Toluenesulfonamide (1.2 g, 7.1 mmol) was added to a solution of Compound 23 (2.0 g, 14 mmol) dissolved in 200 ml of acetonitrile, and the mixture was refluxed at 90° C. for 18 hours. Acetonitrile was evaporated under reduced pressure, and the residue was suspended in 200 ml of water. After the suspension was extracted with methylene chloride, the extract was washed with saturated saline, and then dried over sodium sulfate. Methylene chloride was evaporated under reduced pressure to obtain Compound 24 (2.8 g). Yellow solid. Yield 100%.

$^1$H-NMR (CDCl$_3$, 300 MHz): 7.70 (d, 2H, J=8.2), 7.42 (t, 2H, J=7.7), 7.23 (d, 2H, J=8.2), 7.13 (d, 2H, J=7.7), 6.91 (d, 2H, J=7.7), 4.55 (s, 4H), 2.41 (s, 3H), 2.36 (s, 6H) MASS (FAB): 382 (M$^+$+1)

Compound 24 (2.8 g, 7.3 mmol) was dissolved in 50 ml of sulfuric acid, and then the solution was stirred at 120° C. for 2 hours. The mixture was cooled, then poured into ice water, and neutralized with 2 M aqueous sodium hydroxide. The mixture was extracted with methylene chloride, and the extract was dried over sodium sulfate. Methylene chloride was evaporated under reduced pressure, and purification was carried out by column chromatography on silica gel to obtain Compound 25 (0.64 g). Yellow solid. Yield 39%.

$^1$H-NMR (CDCl$_3$, 300 MHz): 7.53 (t, 2H, J=7.5), 7.17 (d, 2H, J=7.5), 7.02 (d, 2H, J=7.5), 3.97 (s, 4H), 2.54 (s, 6H) MASS (EI): 227 (M$^+$)

Compound 26 (65 mg) was obtained from Compound 4 (0.10 g, 0.12 mmol) and Compound 25 (0.13 g, 0.57 mmol) in the same manner as that of the synthesis of Compound 12. Yellow solid. Yield 55%.

$^1$H-NMR (CDCl$_3$, 300 MHz): 8.06 (d, 2H, J=9.0), 7.96 (d, 2H, J=8.3), 7.54-7.47 (m, 5H), 7.14 (d, 2H, J=7.7), 7.02-7.00 (d, 2H, J=2.2), 7.00 (d, 2H, J=2.2), 6.75 (dd, 2H, J=8.6, 2.2), 6.61 (d, 2H, J=8.6), 6.46 (d, 1H), 3.68-3.65 (m, 6H), 2.68 (t, 2H, J=6.2), 2.47 (s, 6H), 1.37 (s, 18H) MASS (FAB): 954 (M$^+$+1)

Compound 27 (31 mg) was obtained as a 4TFA salt from Compound 26 (65 mg, 0.068 mmol) in the same manner as that of the synthesis of Compound 8. Brown solid. Yield 43%.

$^1$H-NMR (CD$_3$OD, 300 MHz): 7.98-7.93 (m, 2H), 7.61 (d, 1H, J=8.8), 7.57 (d, 2H, J=7.9), 7.44 (d, 2H, J=7.7), 6.69 (dd, 1H, J=8.8, 1.8), 6.66-6.63 (m, 4H), 6.53 (dd, 2H, J=8.8, 2.2), 5.98 (d, 1H, J=1.8), 4.13 (s, 4H), 3.16-3.13 (m, 2H), 2.87-2.83 (m, 2H), 2.52 (s, 6H) MASS (FAB): 601 (M$^+$+1)

Example 6

Synthesis of Compound 28

Compound 13 (11.4 mg, 0.011 mmol) was suspended in 10 ml of acetonitrile, added with cesium carbonate (14.0 mg, 43 µM), and then gradually added with 2.2 ml of acetic anhydride. After the mixture was stirred at room temperature for 1 hour, the reaction solution was evaporated under reduced pressure. Purification was carried out by column chromatography on silica gel to obtain Compound 28 (5.8 mg). White solid. Yield 47%.

$^1$H-NMR (CDCl$_3$, 300 MHz): 8.41-8.36 (m, 2H), 7.72 (d, 1H, J=8.4), 7.47-7.41 (m, 1H), 7.39-7.33 (m, 1H), 7.06 (d, 2H, J=2.2), 7.04-6.98 (m, 3H), 6.99 (d, 2H, J=2.2), 6.85-6.83 (m, 1H), 6.82 (dd, 2H, J=8.6, 2.2), 6.67 (dd, 1H, J=8.4, 1.8), 6.10 (br, 1H), 5.99 (d, 1H, J=1.8), 3.74 (s, 2H), 2.99 (m, 2H), 2.92 (m, 4H), 2.77 (t, 2H, J=4.8), 2.31 (s, 6H) MASS (FAB): 671 (M$^+$+1)

Example 7

Changes in fluorescence intensity by zinc ions were investigated by using Compounds 8, 13, 17, and 22 which were obtained in the aforementioned Examples 1 to 4. The fluorescence intensity of 1 µM of each of the compounds was measured in 100 mM HEPES buffer (pH 7.4). The results are shown in FIG. 1. The fluorescence intensity on the ordinate axis numerically shows changes in fluorescence intensity when the maximum fluorescence intensity variation is taken as 1 by addition of zinc. It was demonstrated that each of the compound gave fluorescence intensity changes in the range of lower concentrations than ZnAF-2 (Compound 12 disclosed in International Publication WO 01/62755). It was further demonstrated that changes in the concentration of zinc ions can be detected in a very wide range of concentrations over $10^{-10}$ M to $10^{-3}$ M by using these five compounds in combination.

Example 8

Figure 2:
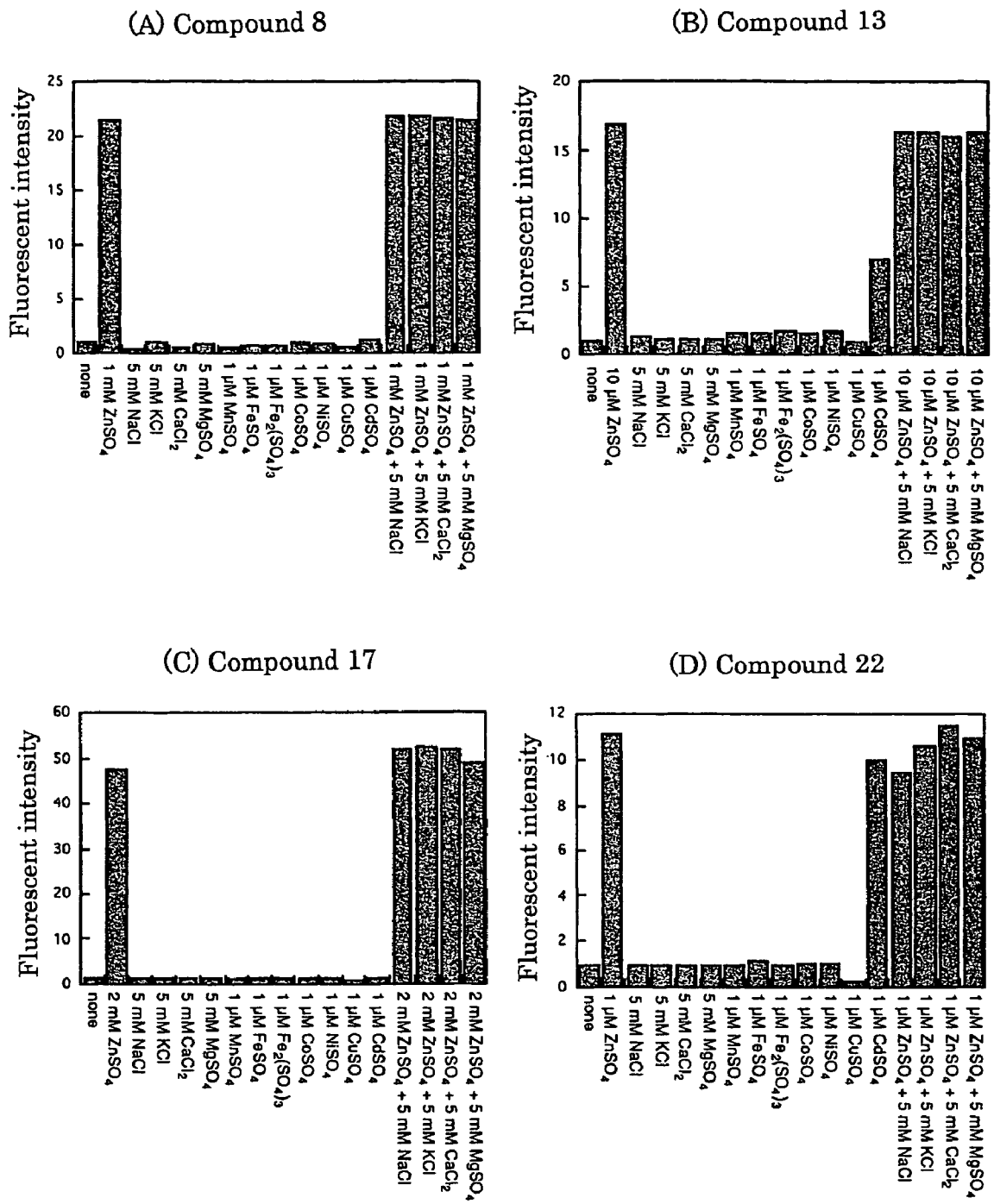
FIG. 2A, B, C, D show changes in fluorescence intensity of each of the test compounds in the presence of a variety of metal ions.

Compounds 8, 13, 17, and 22 were used to evaluate selectivity for zinc ions. 1 µM of the compound was added in 100 mM HEPES buffer (pH 7.5) containing various metal ions (1 µM or 5 µM). The fluorescence intensity was measured at the excitation wavelength of 492 nm and the fluorescence wavelength of 514 nm for Compounds 8, 17, and 22, and the excitation wavelength of 492 nm and the fluorescence wavelength of 521 nm for Compound 13. The results are shown in FIG. 2. In the figure, the ordinate axis shows value of the relative fluorescent intensity measured when each metal ion is added; and in this case, the fluorescence intensity in the absence of metal ion is set to 1. It is clearly understood that Compounds 8, 13, 17, and 22 have extremely high selectivity for zinc ions, and the compounds give absolutely no increase in fluorescence intensity even in the presence of sodium ions, potassium ions, calcium ions, and magnesium ions at high concentration (5 mM), which exist in a living organism. It is also clearly understood that these metal ions do not affect the increase in fluorescence intensity by zinc ions.

Example 9

Figure 3:
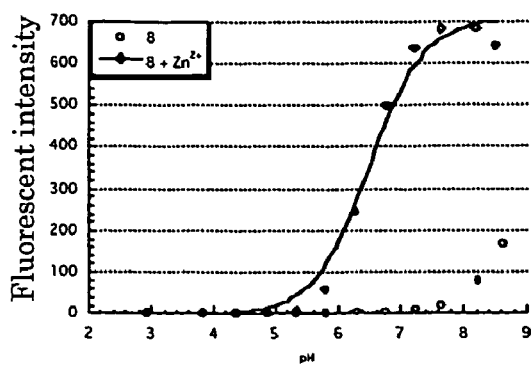
FIG. 3A, B, C, D show changes in fluorescence intensity of each of the test compounds with relation to pH changes.
Figure 3:
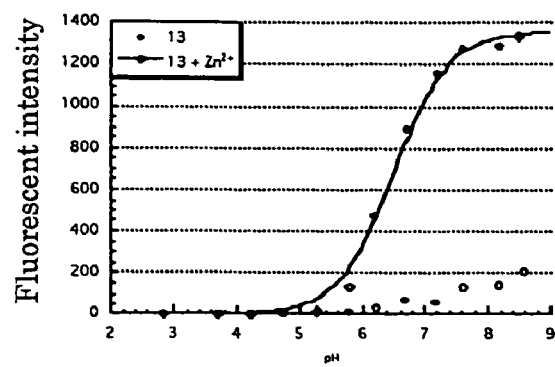
Figure 3:
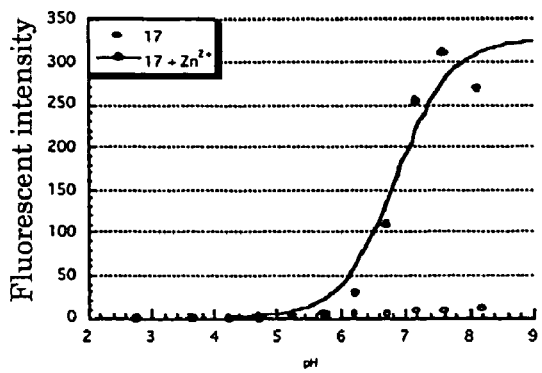
Figure 3:
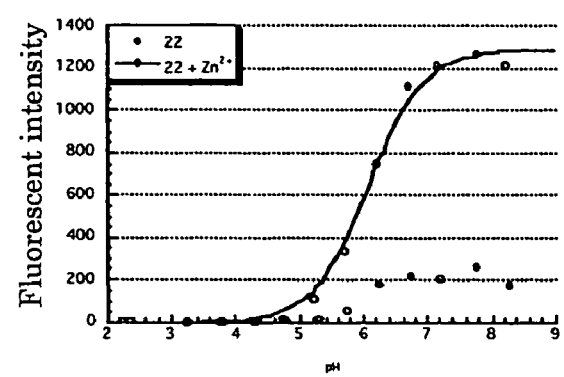
Figure 4:
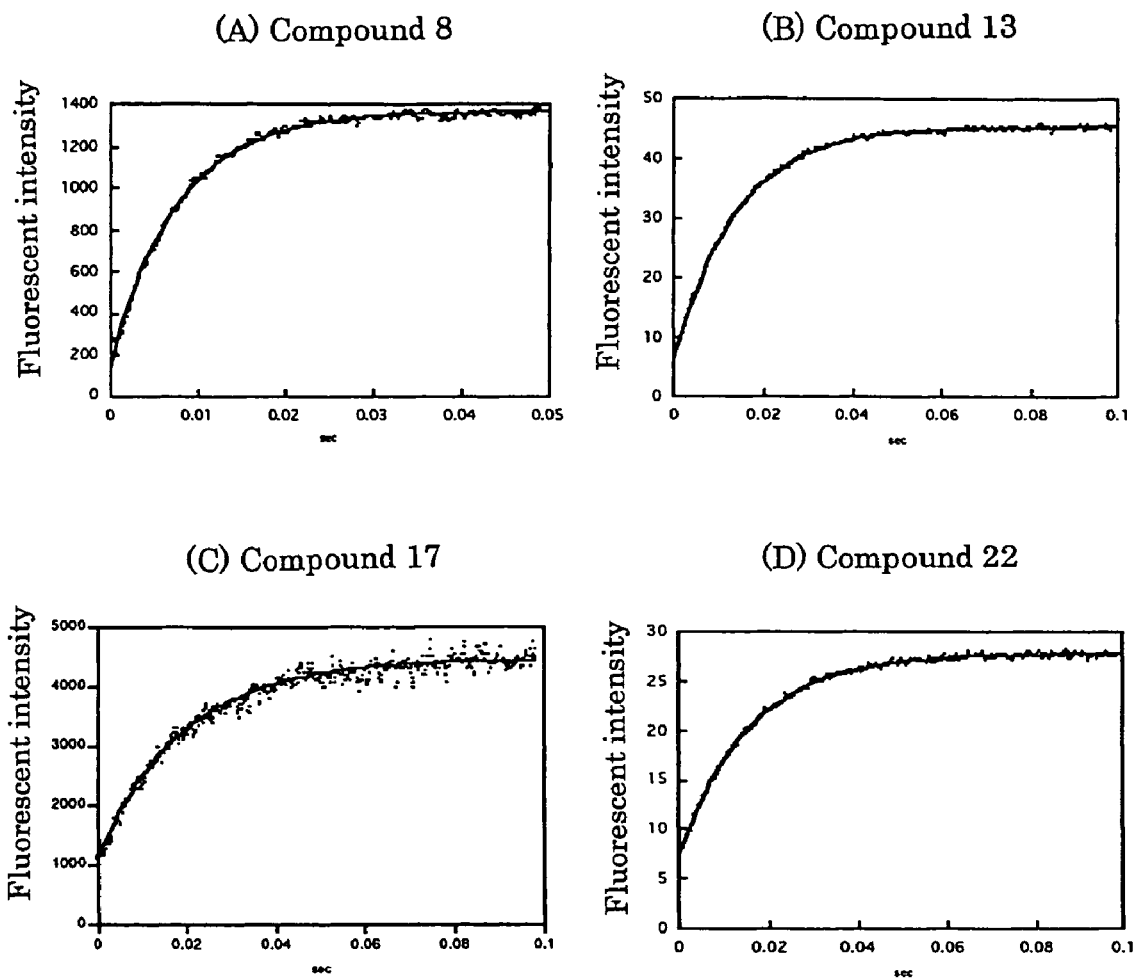
FIG. 4A, B, C, D show the zinc complexing rate between each of the test compounds and zinc ions.
Figure 5:
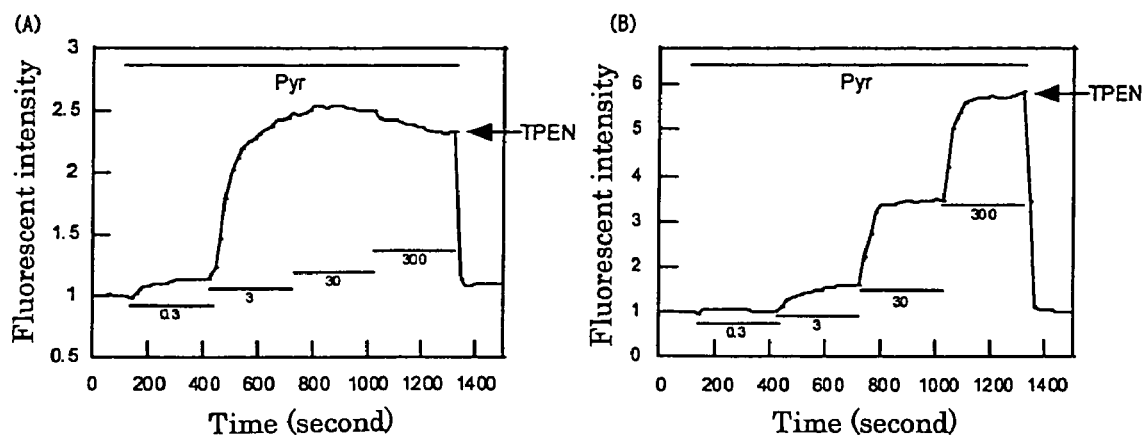
FIG. 5A, B show changes in fluorescence intensity when zinc ions in various concentrations were intracellularly introduced by using CHO cells.

Changes in fluorescence intensity of Compounds 8, 13, 17, and 22, and zinc complexes thereof were investigated with relation to pH changes. The fluorescence intensity was measured at the excitation wavelength of 492 nm and the fluorescence wavelength of 514 nm for Compounds 8, 17, and 22, and the excitation wavelength of 492 nm and the fluorescence wavelength of 521 nm for Compound 13. The results are shown in FIG. 3. Buffers used are as follows.

100 mM $Cl_2CHCOOH$—$Cl_2CHCOONa$ buffer (pH 2.0-2.5)

100 mM $ClCH_2COOH$—$ClCH_2COONa$ buffer (pH 3.0-3.5)

100 mM AcOH—AcONa buffer (pH 4.0-5.0)

100 mM MES buffer (pH 5.5-6.5)

100 mM HEPES buffer (pH 7.0-8.0)

100 mM CHES buffer (pH 8.0-9.0)

It was understood that the fluorescence intensity of all of the compounds was stable at pH of around 7.4 which is an intracellular pH.

Example 10

The rate constant of the formation of a complex between zinc ions and each of Compounds 8, 13, 17, and 22 were investigated. Changes with time of fluorescence intensity were measured in a stopped-flow manner after the compound was mixed in 100 mM HEPES buffer (pH 7.4) at 25° C. to adjust the final concentration of the compound to 1 μM and that of zinc ions to 50 μM. The rate constant of complex formation was calculated by using the graph to give $1.6 \times 10^6$ $M^{-1}s^{-1}$ for Compound 8, $1.4 \times 10^6$ $M^{-1}s^{-1}$ for Compound 13, $7.8 \times 10^4$ $M^{-1}s^{-1}$ for Compound 17, and $1.3 \times 10^6$ $M^{-1}s^{-1}$ for Compound 22. The fluorescence immediately increased by each of the compounds. Therefore, it is understood that zinc ions can be detected in a very short period of time, and rapid changes in the concentration of zinc ions can also be detected by using these compounds.

Example 11

Changes in fluorescence intensity were investigated when zinc ions in various concentrations were intracellularly introduced by using CHO cells. CHO cells were incubated in PBS(−) containing 10 μM ZnAF-2DA (6-[N-[N',N'-bis(2-pyridinylmethyl)-2-aminoethyl]amino-3',6'-bis(acetyloxy)-spiro[isobenzofuran-1(3H),9'-[9H]xanthen]-3-one: Kd value for zinc ions: 2.7 nM) or Compound 28 at room temperature for 10 minutes. After the cells were washed with PBS(−) 3 times, the reagent was added as shown in the following Table 1, and changes in fluorescence intensity were measured.

TABLE 1

| 2 min | 100 μM pyrithione, 0.3 μM $ZnSO_4$ |
| 7 min | 100 μM pyrithione, 3.0 μM $ZnSO_4$ |
| 12 min | 100 μM pyrithione, 30 μM $ZnSO_4$ |
| 17 min | 100 μM pyrithione, 300 μM $ZnSO_4$ |
| 22 min | 300 μM TPEN |

The results were shown in FIG. 1. The results show that fluorescence intensity reached to the plateau of fluorescence intensity when 3 μM zinc ions were introduced to the cells dyed with ZnAF-2DA. In contrast, fluorescence intensity of the cells dyed with Compound 28 increased stepwise with elevation of zinc ions introduced. In other words, the difference of the & value gives the appearance of the difference of intracellular fluorescence intensity. It was understood that Compound 28 was successfully used in the range of higher concentrations of zinc ions than concentrations in which ZnAF-2DA was available.

INDUSTRIAL APPLICABILITY

The compound of the present invention or a salt thereof is useful for measurement of zinc ions. By using the compound of the present invention or a salt thereof, the concentration of zinc ions in a sample in which zinc ions exist in high concentrations be can accurately measured, and a suitable combination of the compounds enables accurate measurement of the concentration of zinc ions in a extremely wide range.

What is claimed is:

1. A compound represented by the following general formula (IB) or a salt thereof:

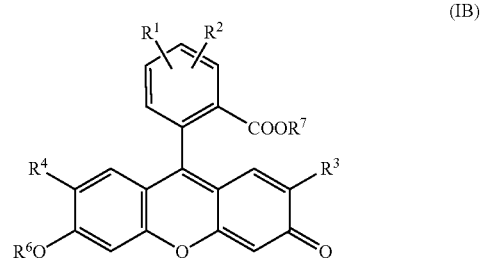

wherein $R^1$ and $R^2$ independently represent a hydrogen atom or a group represented by the following formula (A):

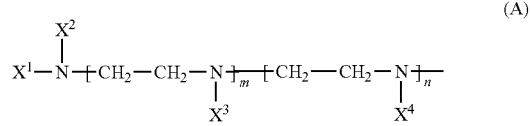

wherein $X^1$, $X^2$, $X^3$, and $X^4$ independently represent a hydrogen atom, a 2-pyridylmethyl group, a 2-pyridylethyl group, a 2-methyl-6-pyridylmethyl group, or a 2-methyl-6-pyridylethyl group, provided that at least one among the groups selected from the group consisting of $X^1$, $X^2$, $X^3$, and $X^4$ represents a group selected from the group consisting of a 2-pyridylethyl group, a 2-methyl-6-pyridylmethyl group, and a 2-methyl-6-pyridylethyl group, and m and n independently represent 0 or 1, provided that m and n do not simultaneously represent 0; provided that $R^1$ and $R^2$ do not simultaneously represent hydrogen atoms; $R^3$ and $R^4$ independently represent a hydrogen atom or a halogen atom; $R^6$ represents a hydrogen atom, an alkylcarbonyl group, or an alkylcarbonyloxymethyl group; and $R^7$ represents a hydrogen atom or an alkyl group.

2. A compound represented by the following general formula (IIB) or a salt thereof:

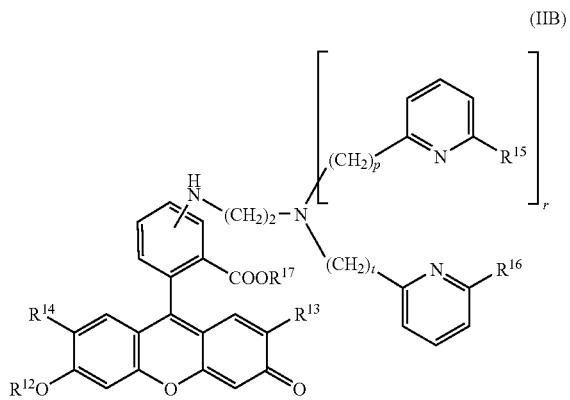

(IIB)

wherein $R^{12}$ represents a hydrogen atom, an alkylcarbonyl group, or an alkylcarbonyloxymethyl group; $R^{13}$ and $R^{14}$ independently represent a hydrogen atom or a halogen atom; $R^{15}$ and $R^{16}$ independently represent a hydrogen atom or a methyl group; $R^{17}$ represents a hydrogen atom or an alkyl group; p and q independently represent 1 or 2; and r represents 0 or 1, provided that when r is 1, it is excluded that $R^{15}$ and $R^{16}$ are simultaneously hydrogen atoms, and p and q are simultaneously 1, and when r is 0, q is 2, and the 2-pyridylalkyl group on the nitrogen is replaced by a hydrogen atom.

3. The compound according to claim 2 or a salt thereof, wherein $R^{13}$ and $R^{14}$ are hydrogen atoms.

4. The compound according to claim 2 or a salt thereof, wherein $R^{17}$ is a hydrogen atom.

5. A fluorescent probe for zinc which comprises a compound represented by the general formula (IB) according to claim 1 or a salt thereof.

6. A zinc complex which is formed by a compound represented by the general formula (IB) according to claim 1 or a salt thereof together with a zinc ion.

7. A method for measuring zinc ions which comprises:
(a) reacting a compound represented by the general formula (IB) according to claim 1 or a salt thereof with zinc ions; and
(b) measuring fluorescence intensity of zinc complex produced in the reacting the compound with zinc ions.

8. A method for measuring zinc ions which comprises measuring zinc ions by using two or more compounds or salts thereof selected from the group consisting of the following (1) to (14) in the following general formula (IIIB):

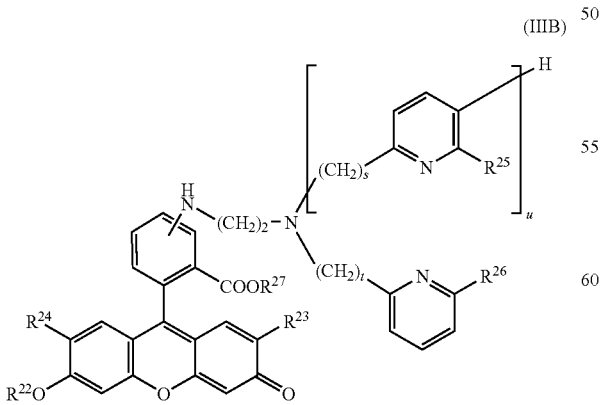

(IIIB)

wherein $R^{22}$ represents a hydrogen atom, an alkylcarbonyl group, or an alkylcarbonyloxymethyl group; $R^{23}$ and $R^{24}$ independently represent a hydrogen atom or a halogen atom; $R^{25}$ and $R^{26}$ independently represent a hydrogen atom or a methyl group; $R^{27}$ represents a hydrogen atom or an alkyl group; s and t independently represent 1 or 2, and u represents 0 or 1, (1) the compound wherein s and t are 1, u is 1, and $R^{25}$ and $R^{26}$ are hydrogen atoms, or a salt thereof
(2) the compound wherein s and t are 1, u is 1, $R^{25}$ is a hydrogen atom, and $R^{26}$ is a methyl group, or a salt thereof
(3) the compound wherein s and t are 1, u is 1, and $R^{25}$ and $R^{26}$ are methyl groups, or a salt thereof
(4) the compound wherein s is 1, t is 2, u is 1, and $R^{25}$ and $R^{26}$ are hydrogen atoms, or a salt thereof
(5) the compound wherein s is 1, t is 2, u is 1, $R^{25}$ is a hydrogen atom, and $R^{26}$ is a methyl group, or a salt thereof
(6) the compound wherein s is 1, t is 2, u is 1, $R^{25}$ is a methyl group, and $R^{26}$ is a hydrogen atom, or a salt thereof
(7) the compound wherein s is 1, t is 2, u is 1, and $R^{25}$ and $R^{26}$ are methyl groups, or a salt thereof
(8) the compound wherein s and t are 2, u is 1, and $R^{25}$ and $R^{26}$ are hydrogen atoms, or a salt thereof
(9) the compound wherein s and t are 2, u is 1, $R^{25}$ is a hydrogen atom, and $R^{26}$ is a methyl group, or a salt thereof
(10) the compound wherein s and t are 2, u is 1, and $R^{25}$ and $R^{26}$ are methyl groups, or a salt thereof
(11) the compound wherein t is 1, u is 0, and $R^{26}$ is a hydrogen atom, or a salt thereof
(12) the compound wherein t is 1, u is 0, and $R^{26}$ is a methyl group, or a salt thereof
(13) the compound wherein t is 2, u is 0, and $R^{26}$ is a hydrogen atom, or a salt thereof
(14) the compound wherein t is 2, u is 0, and $R^{26}$ is a methyl group, or a salt thereof.

9. The method according to claim 8, wherein $R^{23}$, $R^{24}$, and $R^{27}$ are hydrogen atoms.

10. A kit for measuring zinc ions which comprises two or more compounds or salts thereof selected from the group consisting of the compounds (1) to (14) or salts thereof selected from the group consisting of the following (1) to (14) in the following general formula (IIIB):

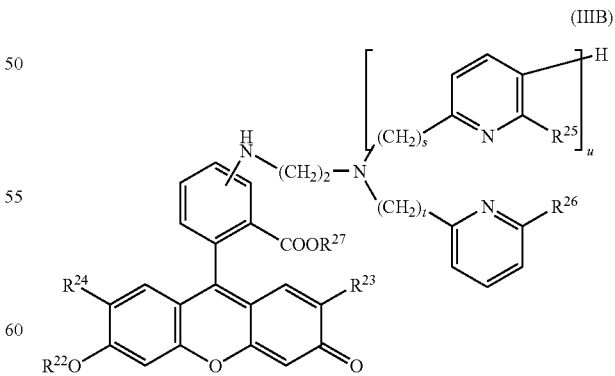

(IIIB)

wherein $R^{22}$ represents a hydrogen atom, an alkylcarbonyl group, or an alkylcarbonyloxymethyl group; $R^{23}$ and $R^{24}$ independently represent a hydrogen atom or a halogen atom; $R^{25}$ and $R^{26}$ independently represent a hydrogen atom or a methyl group; $R^{27}$ represents a hydrogen atom or an alkyl group; s and t independently represent 1 or 2, and u represents 0 or 1, (1) the compound wherein s and t are 1, u is 1, and $R^{25}$ and $R^{26}$ are hydrogen atoms, or a salt thereof
(2) the compound wherein s and t are 1, u is 1, $R^{25}$ is a hydrogen atom, and $R^{26}$ is a methyl group, or a salt thereof
(3) the compound wherein s and t are 1, u is 1, and $R^{25}$ and $R^{26}$ are methyl groups, or a salt thereof
(4) the compound wherein s is 1, t is 2, u is 1, and $R^{25}$ and $R^{26}$ are hydrogen atoms, or a salt thereof
(5) the compound wherein s is 1, t is 2, u is 1, $R^{25}$ is a hydrogen atom, and $R^{26}$ is a methyl group, or a salt thereof
(6) the compound wherein s is 1, t is 2, u is 1, $R^{25}$ is a methyl group, and $R^{26}$ is a hydrogen atom, or a salt thereof
(7) the compound wherein s is 1, t is 2, u is 1, and $R^{25}$ and $R^{26}$ are methyl groups, or a salt thereof
(8) the compound wherein s and t are 2, u is 1, and $R^{25}$ and $R^{26}$ are hydrogen atoms, or a salt thereof
(9) the compound wherein s and t are 2, u is 1, $R^{25}$ is a hydrogen atom, and $R^{26}$ is a methyl group, or a salt thereof
(10) the compound wherein s and t are 2, u is 1, and $R^{25}$ and $R^{26}$ are methyl groups, or a salt thereof
(11) the compound wherein t is 1, u is 0, and $R^{26}$ is a hydrogen atom, or a salt thereof
(12) the compound wherein t is 1, u is 0, and $R^{26}$ is a methyl group, or a salt thereof
(13) the compound wherein t is 2, u is 0, and $R^{26}$ is a hydrogen atom, or a salt thereof
(14) the compound wherein t is 2, u is 0, and $R^{26}$ is a methyl group, or a salt thereof.

11. The compound according to claim 3 or a salt thereof, wherein $R^{17}$ is a hydrogen atom.

* * * * *